US008518559B2

(12) United States Patent
Chen et al.

(10) Patent No.: US 8,518,559 B2
(45) Date of Patent: Aug. 27, 2013

(54) ARYLAMINE COMPOUNDS AND ELECTRONIC DEVICES

(75) Inventors: Zhikuan Chen, Singapore (SG); Changgua Zhen, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 748 days.

(21) Appl. No.: 12/518,089

(22) PCT Filed: Dec. 8, 2006

(86) PCT No.: PCT/SG2006/000383
§ 371 (c)(1),
(2), (4) Date: Jun. 5, 2009

(87) PCT Pub. No.: WO2008/069756
PCT Pub. Date: Jun. 12, 2008

(65) Prior Publication Data
US 2010/0133519 A1    Jun. 3, 2010

(51) Int. Cl.
*H01L 51/54* (2006.01)
(52) U.S. Cl.
USPC ........... 428/690; 428/917; 313/504; 313/506; 252/301.16; 257/40; 257/E51.051; 548/440
(58) Field of Classification Search
USPC .................................................. 257/E51.051
See application file for complete search history.

(56) References Cited

U.S. PATENT DOCUMENTS

| | | | |
|---|---|---|---|
| 5,514,878 A | 5/1996 | Holmes et al. | |
| 6,228,514 B1 | 5/2001 | Tadashi et al. | |
| 6,242,116 B1 | 6/2001 | Tadashi et al. | |
| 6,338,910 B1 | 1/2002 | Ishibashi et al. | |
| 6,514,632 B1 | 2/2003 | Woo et al. | |
| 6,660,410 B2 | 12/2003 | Hosokawa | |
| 6,784,106 B2 | 8/2004 | Bae et al. | |
| 6,791,129 B2 | 9/2004 | Inukai | |
| 7,250,519 B2 | 7/2007 | Stossel et al. | |
| 2002/0093005 A1 | 7/2002 | Sohn et al. | |
| 2003/0048072 A1* | 3/2003 | Ishihara et al. | 313/506 |
| 2003/0157364 A1* | 8/2003 | Senoo et al. | 428/690 |
| 2003/0218418 A9* | 11/2003 | Sato et al. | 313/504 |
| 2003/0230980 A1 | 12/2003 | Forrest et al. | |
| 2005/0089715 A1* | 4/2005 | Cosimbescu et al. | 428/690 |
| 2006/0188745 A1* | 8/2006 | Liao et al. | 428/690 |

FOREIGN PATENT DOCUMENTS

| | | |
|---|---|---|
| EP | 0 875 947 B1 | 11/1998 |
| EP | 0 879 868 A2 | 11/1998 |
| EP | 1 209 952 A2 | 5/2002 |
| EP | 1 442 007 B1 | 10/2002 |
| EP | 1 317 005 A2 | 6/2003 |
| JP | 11035532 | 2/1999 |
| JP | 11 167992 A | 6/1999 |

(Continued)

OTHER PUBLICATIONS

English language machine translation of JP 2001/106678 A, 2001.*
English language machine translation of JP H11-167992 A, 1999.*
Search Report, mailed Jun. 10, 2010, issued in corresponding SG Applicaton No. 200903223-6.
Replaced Written Opinion, mailed Oct. 22, 2010, issued in corresponding SG Application No. 200903223-6.

(Continued)

*Primary Examiner* — Michael H Wilson
(74) *Attorney, Agent, or Firm* — Klarquist Sparkman, LLP

(57) ABSTRACT

There is provided conductive organic arylamine compounds. The compounds may be prepared as films and such films may be used as a hole transporting layer, an emissive layer or an electron transporting layer in organic light emitting devices.

37 Claims, 7 Drawing Sheets

(56) References Cited

FOREIGN PATENT DOCUMENTS

| JP | 11 219787 A | | 8/1999 |
|---|---|---|---|
| JP | 2001/106678 A | * | 4/2001 |
| JP | 2001 106678 A | | 4/2001 |
| JP | 2003013054 | | 1/2003 |
| WO | WO 01/49769 A1 | | 7/2001 |
| WO | WO 02/26859 A1 | | 4/2002 |
| WO | WO 02/043446 A1 | | 5/2002 |
| WO | WO 03/017731 A1 | | 2/2003 |
| WO | WO 03/037844 A1 | | 5/2003 |
| WO | WO 2005/090512 A1 | | 9/2005 |
| WO | WO 2005/105951 A1 | | 11/2005 |

OTHER PUBLICATIONS

Abstract of Publication No. JP 62200-358-A (Canon KK), published Sep. 4, 1987.
OA issued in CN Application No. 200680056860.0 (date of issue May 5, 2011).
English Translation of OA issued in CN Application No. 200680056860.0 (date of issue May 5, 2011).
Written Opinion dated Jun. 16, 2011 (issued in corresponding Singapore Patent Application No. 200903223-6).
Extended European Search Report dated Jul. 12, 2010 (issued in EP Application No. 06824654.5).
1st Examination Report issued in corresponding EP Application No. 06824654.5 (dated Oct. 31, 2011).
Notice of Rejection (dated Jun. 4, 2012) issued in corresponding Japanese Patent Application No. 2009-540210 (with English translation).
Derwent Abstract Accession No. 87-287682/41, (JP 62200-385-A, Canon, KK, Sep. 4, 1987).
Anthopoulos, T.D. et al., "Highly efficient single-layer dendrimer light-emitting diodes with balanced charge transport", Applied Physics Letters, Jun. 30, 2003, pp. 4824-4826, vol. 82, Issue 26.
Barberis, V.P. et al., "Synthesis and optical properties of a poly(p-phenylenevinylene) derivative containing polyfluorenes with bipolar groups among the main chain", Journal of Polymer Science Part A: Polymer Chemistry, Jun. 1, 2006, pp. 3556 3566, vol. 44, Issue 11.
Cha, A.W. and Jin, J.-I., "Electroluminescence of LEDs consisting two layers of Alq3 and high Tg, blue-light emitting branched compounds", Synthetic Metals, May 7, 2004, pp. 97-101, vol. 143, Issue 1.
Deng, L. et al., "Living Radical Polymerization of Bipolar Transport Materials for Highly Efficient Light Emitting Diodes", Chemistry of Materials, Jan. 24, 2006, pp. 386-395, vol. 18, Issue 2.
Higuchi, A. et al., "Amorphous molecular materials: synthesis and properties of a novel starburst molecule, 4,4',4''-tri(N-phenothiazinyl)triphenylamine", Advanced Materials, Nov. 1991, pp. 549-550, vol. 3, Issue 11.
Higuchi, A. and Shirota, Y., "Amorphous molecular materials: synthesis and properties of a novel starburst molecule, 4,4'4''-tri-N-phenoxazinyltriphenylamine", Molecular Crystals and Liquid Crystals Science and Technology, Section A; Molecular Crystals and Liquid Crystals, Mar. 1994, pp. 127-133, vol. 242.
Huang, T.H. et al., "Dipolar Dibenzothiophene S,S-Dioxide Derivatives Containing Diarylamine: Materials for Single-Layer Organic Light-Emitting Devices", Advanced Materials, Mar. 2006, pp. 602-606, vol. 18, Issue 5.
Kim, S.W. et al., "2.4-in. monochrome small molecular OLED display for mobile application", Current Applied Physics., Aug. 2002, pp. 335-338, vol. 2, Issue 4.
Kim, B.S. et al., "Charge mobilities and luminescence characteristics of blue-light emitting bent carbazole trimers connected through vinylene linkers-effect of nitrile substituents", Synthetic Metals, Sep. 2004, pp. 229-235, vol. 145, Issues 2-3.
Kimoto, A. et al., "Synthesis of Asymmetrically Arranged Dendrimers with a Carbazole Dendron and a Phenylazomethine Dendron", Macromolecules, Jul. 27, 2004, pp. 5531-5537.
Kuwabara, Y. et al., "Thermally stable multilayered organic electroluminescent devices using novel starburst molecules, 4,4'4''-tri(N-carbazoyl)triphenylamine (TCTA) and 4,4',4''-tri(3-methylphenylphenylamino)triphenylamine (m-MTDATA), as hole-transport materials", Advanced Materials, Sep. 1994, pp. 677-679, vol. 6, Issue 9.
Lee, M.-T. et al., "Highly Efficient, Deep-Blue Doped Organic Light-Emitting Devices", Advanced Materials, Oct. 2005, pp. 2493-2497, vol. 17, Issue 20.
Liou, G. et al., "Novel high-Tg poly(amine-imide)s bearing pendent N-phenylcarbazole units: synthesis and photphysical, electrochemical and electrochromic properties", Journal of Materials Chemistry, 2006, pp. 1831-1842, vol. 16, Issue 19.
Liu, Y.Q. et al., "Synthesis and characterization of a novel bipolar polymer for light-emitting diodes", Chemical Communications, 1998, pp. 2747-2748, Issue 24.
Liu, Y.Q. et al., "Synthesis and Characterization of a Bipolar Light-Emitting Copolymer Consisting of Tetraphenyldiaminobiphenyl and Bis-Quinoline Units", Chemistry of Materials, Jan. 1999, pp. 27-29, vol. 11, Issue 1.
Liu, Z. et al., "Novel bipolar light-emitting copolymer containing triazole and triphenylamine moieties", Journal of Polymer Science Part A: Polymer Chemistry, Apr. 15, 2002, pp. 1122-1126, vol. 40, Issue 8.
Miteva, T. et al., "Improving the Performance of Polyfluorene-Based Organic Light-Emitting Diodes via Endcapping", Advanced Materials, Apr. 2001, pp. 565-570, vol. 13, Issue 8.
Muller, D.C. et al., "Efficient Blue Organic Light-Emitting Diodes with Graded Hole-Transport Layers", ChemPhysChem, Dec. 15, 2000, pp. 207-211, vol. 1, Issue 4.
Niu, Y. et al., "Thermally crosslinked hole-transporting layers for cascade hole-injection and effective electron-blocking/exciton-confinement in phosphorescent polymer light-emitting diodes", Applied Physics Letters, Feb. 27, 2006, pp. 093505/1-093505/3, vol. 88, Issue 9.
Peng, Z.H. et al., "Polymers with Bipolar Carrier Transport Abilities for Light Emitting Diodes", Chemistry of Materials, Aug. 1998, pp. 2086-2090, vol. 10, Issue 8.
Peng, Z.H. et al., "Toward highly photoluminescent and bipolar charge-transporting conjugated polymers", Macromolecular Symposia, Apr. 2000, pp. 245-252, vol. 154, Issue 1.
Shu, C.F. et al., "Highly Efficient Blue-Light-Emitting Diodes from Polyfluorene Containing Bipolar Pendant Groups", Macromolecules, Sep. 9, 2003, pp. 6698-6703, vol. 36, Issue 18.
Thomas, K.R.J. et al., "Electroluminescent bipolar compounds containing quinoxaline or pyridopyrazine and triarylamine segments", Journal of Materials Chemistry, 2002, pp. 3516-3522, vol. 12, Issue 12.
Thomas, K.R.J. et al., "Color Tuning in Benzo[1,2,5]thiadiazole-Based Small Molecules by Amino Conjugation/Deconjugation: Bright Red-Light-Emitting Diodes", Advanced Functional Materials, Jan. 2004, pp. 83-90, vol. 14, Issue 1.
Wu, F.I. et al., "Highly Efficient Light-Emitting Diodes Based on Fluorene Copolymer Consisting of Triarylamine Units in the Main Chain and Oxadiazole Pendent Groups", Macromolecules, Nov. 1, 2005, pp. 9028-9036, vol. 38, Issue 22.
Zhan, X.W. et al., "A Novel Bipolar Electroluminescent Poly(arylene ethynylene) Consisting of Carbazole and Diethynylthiophene Units", Macromolecular Chemistry and Physics, Jul. 2001, pp. 2341-2345, vol. 202, Issue 11.
Zhang, Y.G. et al., "Polymer light-emitting diodes based on a bipolar transporting luminescent polymer", Journal of Materials Chemistry, 2003, pp. 773-777, vol. 13, Issue 4.
International Search Report (PCT/SG2006/000383), 2010.
International Preliminary Report on Patentability (PCT/SG2006/000383), 2010.
2nd Office Action (date of issue Mar. 26, 2012) issued in Chinese Patent Application No. 200680056860.0.
3rd Office Action issued in Chinese Patent Application No. 200680056860.0 dated Jan. 7, 2013.
1st Office Action issued in Korean Patent Application No. 2009-7011504 dated Jun. 7, 2013.

* cited by examiner

ARYLAMINE COMPOUNDS AND ELECTRONIC DEVICES

FIELD OF THE INVENTION

The present invention relates generally to conductive organic compounds, particularly electroluminescent organic compounds, and to electronic devices containing such compounds.

BACKGROUND OF THE INVENTION

Electroluminescent organic materials can be classified into two categories: conjugated polymers and organic small molecules.

Polymeric electroluminescent organic materials include poly(1,4-phenylenevinylene)s, polyfluorenes, and their derivatives. Electroluminescent polymers are attractive because of their solution processability, which is a relatively cost effective method for manufacturing electronic devices containing electroluminescent organic materials.

However, high purity is difficult to achieve for polymeric light emitting materials since such materials often contain certain amounts of structural defects in the polymer backbone, by-products produced during polymerization, and end groups remaining on the polymer chains. All these impurities and/or defects in preparations of the polymers can affect efficiency and lifespan of electronic devices incorporating polymeric electroluminescent organic materials.

Small molecules represent another category of light emitting materials and have been widely used in organic light emitting devices, such as organic light emitting diodes (OLEDs), either as emitters or as charge transporting materials. It is possible to produce fairly pure small molecule light emitting materials due to use of purification processes such as sublimation or recrystallization process, which provides an advantage compared with light emitting polymers.

However, devices containing small molecules are typically processed using vacuum deposition techniques, which tend not to be cost-effective and which may not be desirable for mass production. Generally, solution processing is a lower cost technique and is more suitable for mass and fast production, and may also be better suited for preparation of larger films that are required for large displays.

Multilayer devices are known, and are typically constructed with a hole transport layer, an emissive layer and an electron transport layer, with possible inclusion of a hole injecting layer and/or electron injecting layer.

However, many of the current organic light emitting materials, both polymers and small molecules, typically have imbalanced charge transporting characteristics. Generally, light emitting materials are able to conduct only one charge carrier, either holes or electrons, but typically not both. For example, poly(1,4-phenylenevinylene)s or alkoxy-substituted poly(1,4-phenylenevinylene)s are good hole transporters, whereas tris-(8-hydroxyquinoline) aluminum (III) (Alq3) is an electron transporter. Imbalanced charge transporting in OLED devices results in low device efficiency.

One solution to balance the charge carriers in the devices, is to combine both electron transport segment and hole transport segment into one structure to construct an ambipolar material; either the two segments are linked together in the backbone or they are attached to the backbone separately.

Although some such ambipolar materials have been developed, to date the reported device performance based on such materials is still not satisfactory.

Thus, there exists a need for new materials that can be used in an organic light emitting layer in an electroluminescent device.

SUMMARY OF THE INVENTION

In one aspect, there is provided a compound of formula (I):

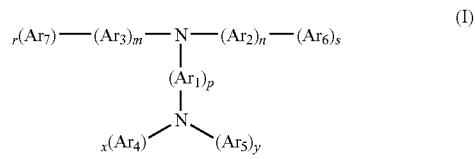

wherein:
each of $Ar_1$, $Ar_2$ and $Ar_3$ is independently arylene; heteroarylene; arylene vinylene; heteroarylene vinylene; arylene ethynylene; or heteroarylene ethynylene, optionally substituted with one or more of branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl;
each of $Ar_4$ and $Ar_5$ is independently arylene; heteroarylene; arylene vinylene; heteroarylene vinylene; arylene ethynylene; or heteroarylene ethynylene, optionally substituted with one or more of branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl;
each of $Ar_6$ and $Ar_7$ is independently arylene; heteroarylene; arylene vinylene; heteroarylene vinylene; arylene ethynylene; or heteroarylene ethynylene, optionally substituted with one or more of branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl and at least one of $Ar_6$ and $Ar_7$ is an electron withdrawing Ar group, is substituted with one or more electron withdrawing substituents, or is an electron withdrawing Ar group substituted with one or more electron withdrawing substituents; and
each of m, n, p, r, s, x and y is independently an integer from 1 to 20.

Embodiments of compounds of formula (I) are electroluminescent, and as such are useful as organic layers in organic electroluminescent devices, and may be used to form the emissive layer, a charge injection layer, a charge transport layer or a hole blocking layer.

Conveniently, the above compounds are composed of both a hole transporting segment and an electron transporting segment, which segments combine to provided the compounds with ambipolar transporting functionality. As well, these compounds are solution processable, and may be readily purified to a relatively high extent.

Thus, in another aspect, there is provided a thin film comprising a compound as described herein.

In a further aspect, there is provided a device comprising an anode, a cathode and a thin film as described herein, the thin film disposed between the anode and the cathode.

In yet a further aspect, there is provided a device comprising: an anode; an emissive layer disposed on the anode, the emissive layer comprising a compound as described herein; and a cathode disposed on the emissive layer.

In another aspect, there is provided a device comprising: an anode; a hole transporting layer disposed on the anode; an emissive layer disposed on the hole transporting layer; an electron transporting layer disposed on the emissive layer; and a cathode disposed on the electron transporting layer; wherein at least one of the hole transporting layer, the emissive layer and the electron transporting layer comprises a compound as described herein.

In still another aspect, there is provided a device comprising: an anode; a hole injecting layer disposed on the anode; a hole transporting layer disposed on the hole injecting layer; an emissive layer disposed on the hole transporting layer; an electron transporting layer disposed on the emissive layer; and a hole blocking layer disposed on the electron transporting layer; an electron injecting layer disposed on the hole blocking layer; a cathode disposed on the electron injecting layer; wherein at least one of the hole transporting layer, the emissive layer or the electron transporting layer comprises a compound as described herein.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
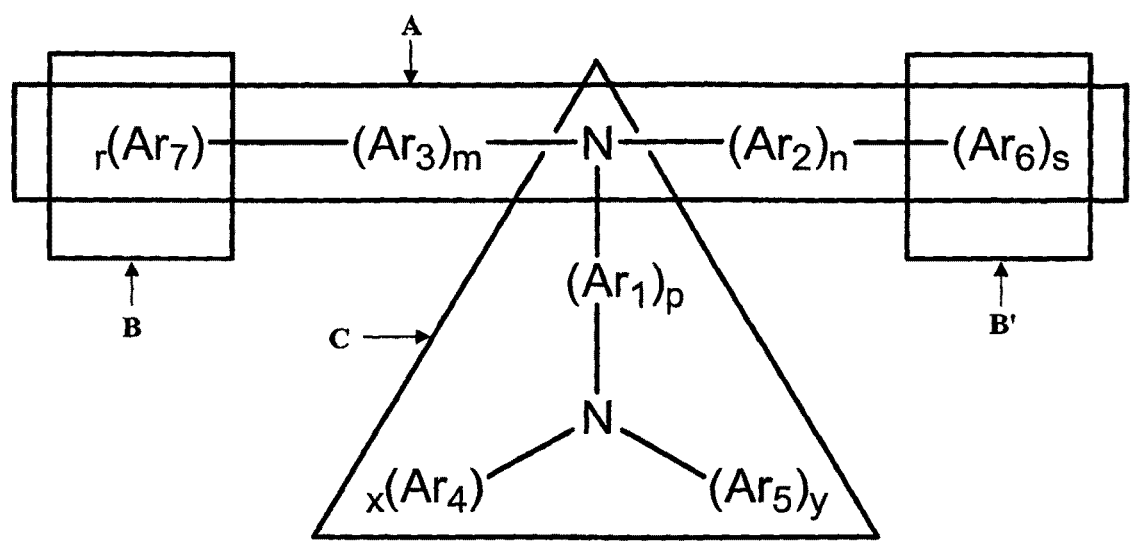
FIG. 1 is a schematic representation of formula (I), indicating the electron transporting, hole transporting and emission tuning segments of formula (I)

Embodiments of compounds of formula (I) described herein are electroluminescent, meaning that these compounds emit light when an electrical current is passed through them. Thus, these compounds are well suited to act as a charge transport layer or a light emitting layer in an organic electronic device.

Certain organic compounds are able to conduct charge due to inclusion of an extensive system of pi bonds in the molecules. That is, compounds with connected or conjugated pi systems, such as polyarylene compounds or polyarylenevinylene compounds (e.g. poly(phenylenevinylene)), have a set of pi molecular orbitals that overlap and extend the length of the molecule. These extended pi molecular orbitals, when unfilled or when only partially filled with electrons, provide channels across the molecule for transport of additional electrons across the molecule when the molecule is placed under a voltage bias. Several such extended pi orbitals can form across a conductive organic compound, each having different structure and energy levels. The molecular orbital having the lowest energy level is often an effective path for transport of extra electrons.

In order for these compounds to luminesce, as an electron is being transported across the molecule, one or more electrons must move from a filled or partially filled higher energy orbital to an unfilled or partially filled lower energy orbital. If the energy released by the electron as it passes from a high energy state to a low energy state is in the visible spectrum, these molecules are seen to emit light.

Briefly, when a hole is injected into a conductive organic molecule, the molecule becomes positively charged, and conversely when an electron is injected into such a molecule, it becomes negatively charged. A charged molecule can obtain an opposite charge from an adjacent molecule, resulting in charge transport in a composition containing the conductive organic molecule. An injected electron and hole can recombine within the emissive layer, forming a bound electron/hole pair, termed an exciton, which can emit energy when it relaxes from an excited state to a lower energy state. Depending on the wavelength of the emitted energy, the energy may be released as ultraviolet or visible light.

The described compounds are relatively small molecules when compared with organic polymers, and can readily be purified to a relatively high degree following preparation, for example by column chromatography or by crystallization from solution, resulting in a final compound of higher purity than a polymer, and which is relatively free of unreacted starting reagents and intermediates. Thus, inclusion of these compounds as a charge transporting or light emitting layer in organic electronic devices may result in a device that has a longer life span and that is more efficient in terms of charge transport.

The present compounds possess both electron transporting and hole transporting regions, and thus are ambipolar in terms of charge transport. As a result, these compounds have balanced charge transporting properties and thus are particularly suited for inclusion in an organic light emitting device, such as an OLED.

As shown in FIG. 1, the present compounds incorporate a segment that can be designed and selected so as to control the emission wavelength of the compound (labelled A in FIG. 1). The segment defined by $Ar_7$, $Ar_3$, $Ar_2$ and $Ar_6$ may vary with respect to the nature of the Ar groups, the number of Ar groups, and the nature of any substituents attached to one or more of the Ar groups. Each of these factors helps to determine the emission wavelength of a particular compound of formula (I).

As well, the compounds of formula (I) have one or more electron withdrawing groups incorporated (labelled B and B' in FIG. 1), to provide electron transporting properties to the compounds. At least one of $Ar_6$ and $Ar_7$ and optionally one or more of $Ar_2$ and $Ar_3$ is an electron withdrawing group or is substituted with electron withdrawing substituent. Incorporation of one or more electron withdrawing group enhances electron injection and transporting in the light emissive layer, which may be able to improve the device efficiency of organic light emitting devices incorporating these compounds.

These compounds also have a central tertiary nitrogen, substituted with three Ar groups, $Ar_1$, $Ar_2$ and $Ar_3$ (this portion is labelled C in FIG. 1). Of the three Ar groups attached to the central nitrogen, at least $Ar_1$ is further connected to another nitrogen atom. Such a design assists in increasing the energy level of the highest occupied molecular orbital (HOMO) of the compound, thus facilitating the hole injection and hole transport properties of the compounds. As well, this design may result in decreased turn-on voltage and the operational voltage for electronic devices incorporating the compounds of formula (I).

The present compounds are thus described by formula (I), which is set out below.

In the context of formula (I) and as used herein, an "arylene" group is a bivalent aromatic radical derived from an aromatic compound by removal of two hydrogen atoms. An aromatic compound is a cyclic compound having 4n+2 pi electrons where n is an integer equal to or greater than 0. In certain embodiments, the arylene group may have from 5 to 100 backbone carbon atoms, from 5 to 60 backbone carbon atoms, from 5 to 50 backbone carbon atoms, from 5 to 30 backbone carbon atoms, or from 5 to 20 backbone carbon atoms.

An "aryl" group as used herein is a monovalent aromatic radical derived from an aromatic compound by removal of one hydrogen atom. An aromatic compound is a cyclic compound having 4n+2 pi electrons where n is an integer equal to or greater than 0. In certain embodiments, the aryl group may have from 5 to 100 backbone carbon atoms, from 5 to 60 backbone carbon atoms, from 5 to 50 backbone carbon atoms, from 5 to 30 backbone carbon atoms, or from 5 to 20 backbone carbon atoms.

A "heteroarylene" group as used herein is an arylene group in which one or more of the backbone carbon atoms has been replaced with a hetero atom, including N, O, S, Si or P.

A "heteroaryl" group as used herein is an aryl group in which one or more of the backbone carbon atoms has been replaced with a hetero atom, including N, O, S, Si or P.

It will be appreciated that where a particular Ar group is described as including an arylene or heterarylene group, but where such an arylene or heteroarylene occurs at an end of the molecule and is monovalent, that the particular group will be aryl or heteroaryl. For example, if $Ar_6$ is described as including an arylene or heteroarylene group and s is 2, then the terminal $Ar_6$ group in $(Ar_6)_s$ will include an aryl or heteroaryl group (provided it is not bonded or linked to another Ar group), but the penultimate $Ar_6$ group will include an arylene or heteroarylene group.

A "vinylene" group as used herein is the bivalent radical represented by the formula —CH=CH—.

An "ethynylene" group as used herein is the bivalent radical represented by the formula —C≡C—.

Thus, the symbol "Ar" as used herein refers generally to an aryl group, an arylene group, a heteroaryl group, a heteroarylene group, an aryl group and an adjacent vinylene group ("aryl vinylene"), an arylene group and an adjacent vinylene group ("arylene vinylene"), a heteroaryl group and an adjacent vinylene group ("heteroaryl vinylene"), a heteroarylene group and an adjacent vinylene group ("heteroarylene vinylene"), an aryl group and an adjacent ethynylene group ("aryl ethynylene"), an arylene group and an adjacent ethynylene group ("arylene ethynylene"), a heteroaryl group and an adjacent ethynylene group ("heteroaryl ethynylene"), or a heteroarylene group and an adjacent ethynylene group ("heteroarylene ethynylene").

An "alkyl" group as used herein refers to a branched or unbranched monovalent hydrocarbon group, having 1 to 18 carbon atoms. Similarly, an "alkylene" group as used herein refers to a branched or unbranched bivalent hydrocarbon group, having 1 to 18 carbon atoms. It will be understood that alkenyl and alkenylene are the respective terms for a monovalent and bivalent hydrocarbon radical that contains one or more double bonds and that alkynyl and alkynylene are the respective terms for a monovalent and bivalent hydrocarbon radical that contains one or more triple bonds.

Thus, in one aspect there is provided a compound of formula (I):

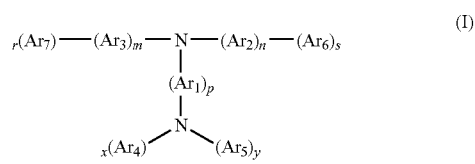

In the above formula (I), each of $Ar_1$, $Ar_2$ and $Ar_3$ is independently an arylene group; a heteroarylene group; an arylene vinylene group; a heteroarylene vinylene group; an arylene ethynylene group; or a heteroarylene ethynylene group; any of which may be further substituted with one or more of: branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl group.

Optionally, at least one of $Ar_2$ and $Ar_3$ may be independently substituted with one or more electron withdrawing substituents. An "electron-withdrawing substituent" is a substituent that has a tendency to pull electrons away from the backbone of the group on which it is substituted, towards the substituent, creating an electron-rich region at or near the substituent. Electron-withdrawing substituents include halo, perfluoroalkyl, carbonyl, carboxyl, cyano, ammonio, nitro, thionyl, sulfonyl, amido linked to the backbone through the oxygen, pyridinium, phosphonium, pyridyl, thiazolyl, oxadiazolyl and triazolyl groups.

In particular embodiments, at least one of $Ar_2$ and $Ar_3$ comprises 9,9-dialkylfluorenylene. In particular embodiments, the 9,9-dialkylfluroenylene is 9,9-dihexylfluorenylene. In other particular embodiments, each of $Ar_2$ and $Ar_3$ comprises 9,9-dialkylfluorenylene. In yet other particular embodiments, each of $Ar_2$ and $Ar_3$ comprises 9,9-dihexylfluorenylene. In yet other particular embodiments, each of $Ar_2$ and $Ar_3$ is 9,9-dihexylfluorenylene.

In particular embodiments, $Ar_1$ is phenylene.

Each of $Ar_4$ and $Ar_5$ is independently an arylene group; a heteroarylene group; an arylene vinylene group; a heteroarylene vinylene group; an arylene ethynylene group; or a heteroarylene ethynylene group; any of which may be further substituted with one or more of: branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl group. As mentioned above, for terminal Ar groups within $Ar_4$ or $Ar_5$, the terminal Ar group will comprise an aryl or heteroaryl group as opposed to arylene or heteroarylene.

Furthermore, one or more of $Ar_1$, $Ar_4$ and $Ar_5$ may be optionally independently substituted with one or more of: alkylthio, amino, hydroxyl, amido connected to the backbone through the nitrogen, carboxyl connected to the backbone through the oxygen, phenyl, naphthyl, thienyl, furyl, pyrrolyl and carbazolyl.

In particular embodiments, at least one of $Ar_4$ and $Ar_5$ is phenyl. In other particular embodiments, each of $Ar_4$ and $Ar_5$ is phenyl.

Furthermore, optionally one or more of the pairs of $Ar_1$ and $Ar_2$; $Ar_1$ and $Ar_3$; $Ar_2$ and $Ar_3$; $Ar_4$ and $Ar_5$; $Ar_1$ and $Ar_4$; and $Ar_1$ and $Ar_5$ may be connected between the two Ar groups in the pair via a single bond or via a linking group including O, S, Si, branched or unbranched, substituted or unsubstituted alkylene, branched or unbranched, substituted or unsubstituted alkenylene, branched or unbranched, substituted or unsubstituted alkynylene, as a connecting group. Thus, it will be appreciated that for example where $Ar_4$ or $Ar_5$ is connected to another Ar group, then the particular $Ar_4$ or $Ar_5$ will be a bivalent group rather than monovalent. For example, if $Ar_4$ is connected to $Ar_1$ by a linking group, then $Ar_4$ would be for example an arylene group rather than an aryl group. It will also be appreciated that where any of m, n, p, r, s, x or y is greater than 1, then the linking may occur between any two of the possible Ar groups. For example, if $Ar_1$ and $Ar_2$ are linked, and if p and n are both 2, then either of the $Ar_1$ groups may be linked to either of the $Ar_2$ groups. As well, it is possible that more than one of the $Ar_1$ groups may be linked to one or more of the $Ar_2$ groups.

In particular embodiments, $Ar_4$ and $Ar_5$ are connected to each other by a single bond. In particular embodiments, each of $Ar_4$ and $Ar_5$ is phenylene and $Ar_4$ and $Ar_5$ are connected to each other by a single bond.

Each of $Ar_6$ and $Ar_7$ is independently an arylene group; a heteroarylene group; an arylene vinylene group; a heteroarylene vinylene group; an arylene ethynylene group; or a heteroarylene ethynylene group; any of which may be substituted with one or more of: branched or unbranched alkyl, branched or unbranched heteroalkyl, branched or unbranched alkenyl, branched or unbranched heteroalkenyl, branched or unbranched alkynyl, branched or unbranched heteroalkynyl, branched or unbranched alkoxy, aryl and heteroaryl group. As mentioned above, for terminal Ar groups within $Ar_6$ or $Ar_7$, the terminal Ar group will comprise an aryl or heteroaryl group as opposed to arylene or heteroarylene.

Additionally, at least one of $Ar_6$ and $Ar_7$ is an electron withdrawing Ar group and/or is substituted with one or more electron withdrawing substituents.

An "electron withdrawing Ar group" refers to an electron-deficient Ar group or an Ar group substituted with one or more electron withdrawing substituents so as to have a tendency to accept or attract electrons from adjacent Ar groups along the backbone. For example, pyridylene, thiazolylene, oxadiazolylene and triazolylene are electron-deficient Ar groups. Electron-withdrawing substituents include halo, perfluoroalkyl, carbonyl, carboxyl, cyano, ammonio, nitro, thionyl, sulfonyl, amido linked to the backbone through the oxygen, pyridinium, phosphonium, pyridyl, thiazolyl, oxadiazolyl and triazolyl groups.

The ability of an electron withdrawing Ar group to withdraw electrons from a neighbouring Ar group tends to make an electron-withdrawing Ar group more electron-dense than a neighbouring Ar group that is not electron-withdrawing, similar to n-type materials used in a Si semiconductor, and thus more able to transport electrons. Generally, electron-withdrawing groups are groups that create a positive or delta-positive region adjacent to the backbone so as to pull electrons from the backbone toward the substituent.

In certain embodiments, at least one of $Ar_6$ or $Ar_7$ is substituted with one or more electron withdrawing substituents, wherein an electron withdrawing substituent includes halo, perfluoroalkyl, carbonyl, carboxyl, cyano, ammonio, nitro, thionyl, sulfonyl, amido linked to the backbone through the oxygen, pyridinium, phosphonium, pyridyl, thiazolyl, oxadiazolyl and triazolyl groups.

In certain embodiments, at least one of $Ar_6$ or $Ar_7$ is one or more of the following Ar groups, in which each of R, R', R" and R'" is independently halo, cyano, nitro, carbonyl, thionyl, sulphonyl, allyl, perfluoroalkyl, alkoxy, aryl, arylene vinylene, or arylene ethynylene, and q is an integer from 0 to 6.

It will be appreciated that although certain of the Ar groups below are depicted as either monovalent or bivalent, any of groups may be either monovalent or bivalent, depending on the context in which the Ar group occurs in the compound, as described above. As well, certain of the compounds are depicted with the bond that attaches the group to the remaining portion of the compound as entering into the center of the Ar group ring, either at an atom or across a bond. It will be appreciated that such depiction is intended to represent that the particular Ar group may be attached to the remaining portion of the compound by a bond at any available position on the ring.

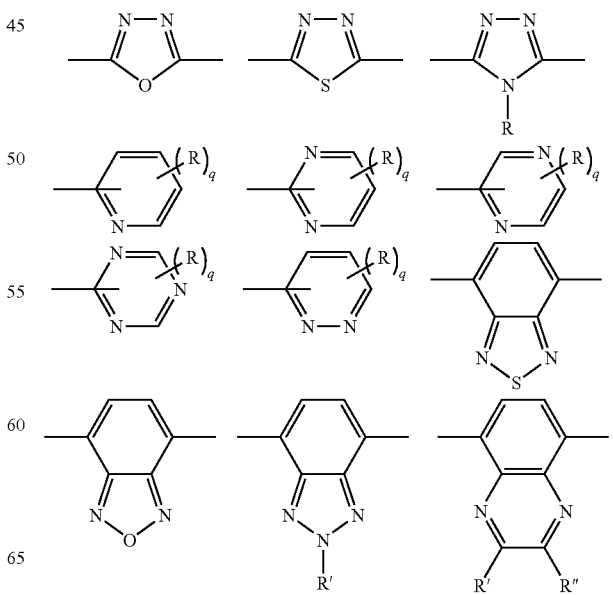

-continued

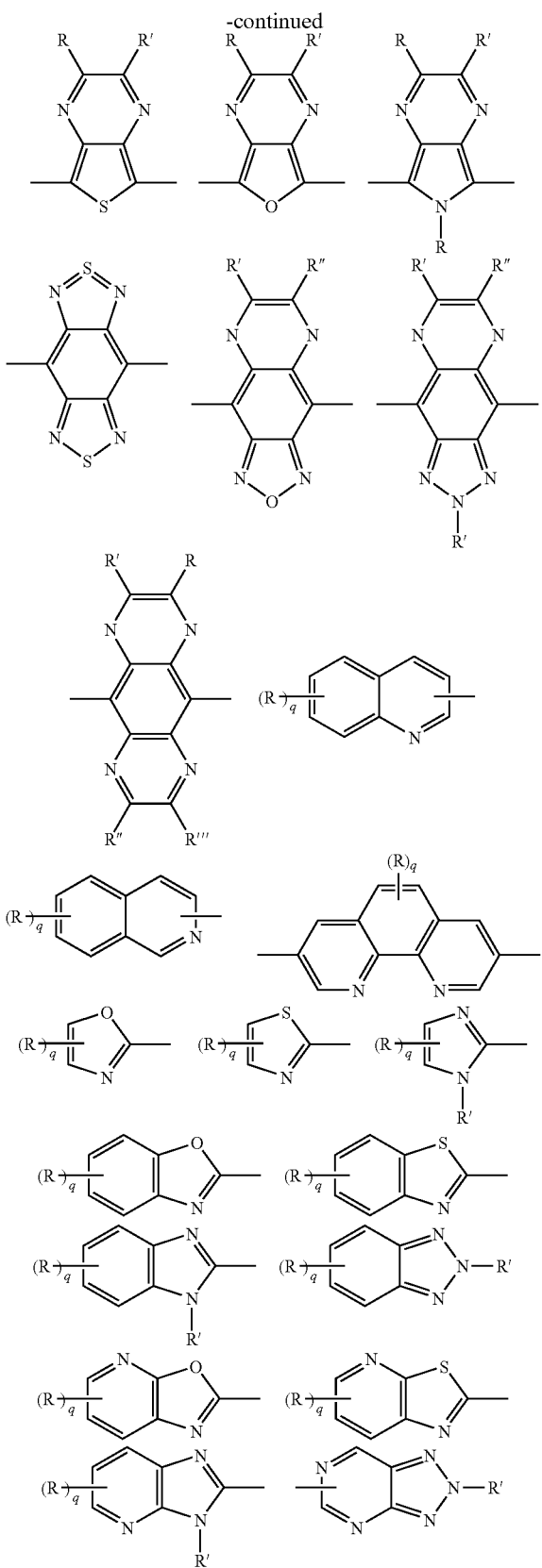

Each of m, n, p, r, s, x and y is independently an integer from 1 to 20. As such, it should be understood that each of m, n, p, r, s, x and y can be any number between 1 to 20 and any range within 1 to 20, such as for example, from 1 to 15, from 1 to 10 or from 1 to 5, or from 10 to 15 or from 10 to 20. If any one of m, n, p, r, s, x or y is greater than one, then the relevant Ar group (for example $Ar_7$ for r) is chosen independently for each occurrence of that Ar group. For example, where r is 5, each of the 5 $Ar_7$ groups is chosen independently from the remaining 4 $Ar_7$ groups.

In particular embodiments, at least one of $Ar_6$ and $Ar_7$ is phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl or 7-(4'-cyanophenyl)-9,9-dihexylfluorenyl. In particular embodiments, $Ar_6$ and $Ar_7$ are the same, and both are phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl or 7-(4'-cyanophenyl)-9,9-dihexylfluorenyl.

In particular embodiments, $Ar_1$ is phenylyene, $Ar_2$ and $Ar_3$ are both 9,9-dihexylfluorenylene, $Ar_4$ and $Ar_5$ are both phenylene and are connected to each other by a single bond, $Ar_6$ and $Ar_7$ are the same and both are phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl or 7-(4'-cyanophenyl)-9,9-dihexylfluorenyl, and each of m, n, p, r, s, x and y is 1.

The compounds of formula (I) can be synthesized using standard organic synthesis techniques known in the art. Examples of suitable synthesis mechanisms are set out in FIG. 2 and in the Examples as set out below. For example, the Ullmann reaction may be applied to couple an aromatic halide with an aromatic amine. As well, the Grignard reaction, the Stille reaction and the Suzuki coupling reaction may be used to link two aromatic functional groups.

As stated above, compounds of formula (I) can be purified by standard methods, such as column chromatography or by crystallization from solution. Such techniques are known and a skilled person will readily be able to apply such techniques to the compounds of formula (I), with minimal routine effort.

The compounds as described herein are suitable for solution processing, thus allowing for production of a thin film containing the compounds. Thus, in one aspect there is provided a thin film comprising a compound of formula (I).

The thin film is a thin layer containing a compound of formula (I), which may be formed to be in the order of from about 0.1 to about 1000 nm thick, from about 1 to about 500 nm thick, from about 5 to about 250 nm thick, or from about 5 to about 100 nm thick.

The thin film may contain other components. For example, the thin film may comprise a host material such as a conductive organic chemical, and a compound of formula (I). The host material may be for example poly(9-vinylcarbazole) (PVK), 4,4'-N,N'-dicarbazole-biphenyl (CBP), 4,4',4"-tri(N-carbazole)triphenylamine (TCTA), N,N'-diphenyl-N,N'-bis(3-methylphenyl)(1,1'-biphenyl)-4,4'-diamine (TPD), N,N'-bis(1-naphthyl)-N,N'-diphenyl-1,1'''-biphenyl-4,4'-diamine (NPB), 4,4',4"-tris(N,N-diphenyl-amino). triphenylamine (TDATA), 1,3,5-tris(diphenylamino)benzene (TDAB), 1,3,5-tris(4-(di-2-pyridylamino)phenyl)benzene (TDAPB), TTBND, PPD, PTDATA, BFA-1T, p-dmDPS, p-DPA-TDAB, MTBDAB, spiro-mTTB, DBC, poly(1,4-phenylenevinylene), polyfluorene, poly(styrenesulfonic acid), poly(3,4-ethylenedioxythiophene), polyacetylene, polypyrrole, polyaniline, 3-phenyl-4(1' napthyl)-5-phenyl-1,2,4-triazole (TAZ), 2-(4-biphenyl)-5(4-tertbutyl-phenyl)-1,3,4,oxadiazole (PBD), 1,3,4-oxadiazole,2,2'-(1,3-phenylene)bis[5-[4-(1,1-dimethylethyl)phenyl]] (OXD-7) or poly[2-(6-cyano-6-methyl)heptyloxy-1,4-phenylene(CNPP), AlOq, Alq(Clq)2, Al(Saph-q), Al(ODZ)3, Ph2Bq, Zn(BIZ)2, Bepp2, Bebq2, Zn(ODZ)2, spiro-PBD, BMB-3T.

The ratio of the host to the compound of formula (I) may be from about 100:0.01 to about 0.01:100.

Alternatively, the thin film may comprise a compound of formula (I) as a host material and may further comprise an organic dye or phosphorescent emitter, for example, dyes such as 10-(2-benzothiazolyl)-1,1,7,7-tetramethyl-2,3,6,7-tetrahydro-1H,5H,11H-[1]benzo-pyrano[6,7,8-ij]quinolizin-11-one, 3-(2-benzothiazolyl)-7-(diethylamino)-2H-1-benzopyran-2-one, 4-(dicyanomethylene)-2-t-butyl-6-(1,1,7,7-tetramethyljulolidyl-9-enyl)-4H-pyran (DCJTB), rubrene, 4-(dicyanomethylene)-2-t-butyl-6-(p-diphenylaminostyryl)-4H-pyran (DCTP), 3-(dicyanomethylene)-5,5-dimethyl-1-[(4-dimethylamino)styryl]cyclohexene (DCDDC), 6-methyl-3-[3-(1,1,6,6-tetramethyl-10-oxo-2,3,5,6-tetrahydro-1H,4H,10H-11-oxa-3a-azabenzo[de]-anthracen-9-yl)acryloyl]pyran-2,4-dione (AAAP), 6,13-diphenylpentacene (DPP) and 3-(N-phenyl-N-p-tolylamino)-9-(N-p-styrylphenyl-N-p-tolylamino)perylene [(PPA)(PSA)Pe-1], 1,1'-dicyano-substituted bis-styrylnaphthalene derivative (BSN), or phosphorescent emitters such as PtOEP, Ir(ppy)3 or their derivatives.

The ratio of the disclosed compounds to the dye or the phosphorescent emitter is from about 100:0.01 to about 1:1.

The thin film may be formed on a suitable substrate, which may be any solid substrate, including quartz, glass, mica, a plastic substrate such as polyethylene terephthalate or polycarbonate, paper, metal, or silicon. The thin film may also be layered onto another layer when forming a multilayered device, or onto an electrode.

To form the thin film, the compound of formula (I) and any additional film components may be dissolved in a suitable organic solvent. Suitable solvents include chloroform, toluene, xylene, ethyl benzoate, 1,1,2,2-tetrachloroethane, THF, dichlorobenzene, mesitylene and mixtures of the aforesaid solvents.

The thin film may be formed on a suitable surface using standard deposition or coating methods including solution coating. Solution coating includes spin coating, casting, microgravure coating, gravure coating, bar coating, roll coating, wire bar coating, dip coating, spray coating, screen printing, flexo printing, offset printing and inkjet printing.

The compounds of formula (I) and thin films containing such compounds may be used to construct electroluminescent devices, including single layer and multilayer devices. The compounds of formula (I) and thin films containing such compounds may form the emissive layer in an organic light emitting diode, the active layer in an organic thin film transistor or the active layer in an organic photovoltaic cell. Such devices and layers are known in the art.

Thus, in another aspect, there is provided a device comprising a compound of formula (I) or a thin film comprising a compound of formula (I).

Figure 3:
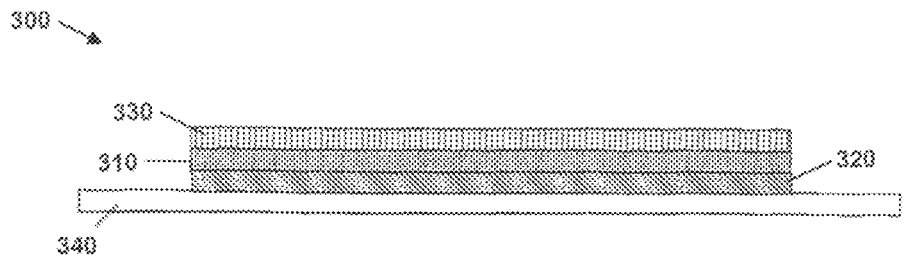
FIG. 3 is a representation of a single layer device incorporating a thin film containing a compound of formula (I)

In one embodiment, with reference to FIG. 3, device 300 comprises an emissive layer 310 comprising a compound of formula (I). As stated above, emissive layer 310 may further include a host material in addition to the compound of formula (I).

Emissive layer 310 is disposed between an electron injecting cathode 320 and a hole injecting anode 330.

The anode 330 is any material capable of conducting holes and injecting them into organic layers. Anode 330 may be gold, silver or indium tin oxide (ITO), or conductive polymer layers. The anode 330 may be reflective, transparent, semi-transparent or translucent.

Cathode 320 is any material capable of conducting electrodes and injecting them into organic layers. Cathode 320 may be a low work function metal or metal alloy, including, for example, barium, calcium, magnesium, indium, aluminum, ytterbium, a calcium: silver alloy, an aluminum:lithium alloy, or a magnesium:silver alloy, such as, for example an alloy wherein the atomic ratio of magnesium to silver is about 10:1 (U.S. Pat. No. 6,791,129) or an alloy where the atomic ratio of lithium to aluminum is about 0.1:100 to about 03:100 (Kim et al. (2002) *Curr. Appl. Phys.* 2(4):335-338; Cha et al (2004) *Synth. Met.* 143(1): 97; Kim et al (2004) *Synth. Met.*145(2-3): 229). The cathode 320 may be a single layer or have a compound structure. Cathode 320 may comprise layers of lithium fluoride, aluminium and silver. The cathode 320 may be reflective, transparent, semi-transparent or translucent.

In certain embodiments, one or more of the anode and the cathode may be deposited on a support 340, which may be transparent, semi-transparent or translucent. Support 340 may be rigid, for example quartz or glass, or may be a flexible polymeric substrate. Examples of flexible transparent semi-transparent or translucent substrates include, but are not limited to, polyimides, polytetrafluoroethylenes, polyethylene terephthalates, polyolefins such as polypropylene and polyethylene, polyamides, polyacrylonitrile and polyacrionitrile, polymethacrylonitrile, polystyrenes, polyvinyl chloride, and fluorinated polymers such as polytetrafluoroethylene.

Figure 4:
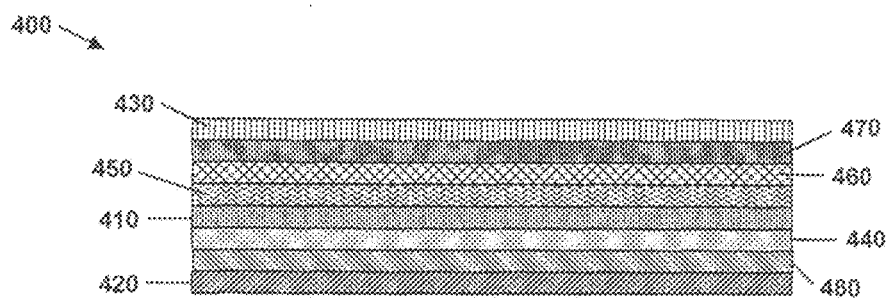
FIG. 4 is a representation of a multi layer device incorporating at least one thin film containing a compound of formula (I)

The device may comprise further additional layers. In one embodiment, as depicted in FIG. 4, the device 400 is an organic light emitting diode (OLED).

Thus, device 400, in addition to emissive layer 410, device 400 includes anode 420 and cathode 430.

Disposed between anode 420 and emissive layer 410, device 400 includes a hole transporting layer 440. The hole transporting layer 440 comprises a hole transporting material, which is any material that can transport holes from the anode 420 into the emissive layer 410. Suitable hole transporting materials include for example a mixture of poly(3,4-ethylenedioxythiophene) and poly(styrenesulfonic acid), or may be polyaniline.

Optionally, a hole injecting layer 480 may be included between anode 420 and hole transporting layer 440. Hole injecting layer 480 comprises a hole injecting material, such as 4,4'-N,N'-dicarbazole-biphenyl (CBP), 4,4',4"'-tri(N-carbazole)triphenylamine (TCTA), N,N'-diphenyl-N,N'-bis(3-methylphenyl)(1,1'-biphenyl)-4,4'-diamine (TPD), N,N'-bis (1-naphthyl)-N,N'-diphenyl-1,1"'-biphenyl-4,4'-diamine (NPB), TDATA, TDAB, TDAPB, TTBND, PPD, PTDATA, BFA-1T, p-dmDPS, p-DPA-TDAB, MTBDAB, spiro-mTTB, DBC, poly(1,4-phenylenevinylene) or its derivatives, or polyfluorene or its derivatives.

Device 400 may optionally include an electron transporting layer 450 disposed between emissive layer 410 and the cathode 430. Electron transporting layer 450 comprises an electron transporting material, which is any material that can transport electrons from the cathode 430 to the emissive layer 410. Electron transporting materials are known to a skilled person and include aluminum tris(8-hydroxyquinoline), 2-(4-biphenyl)-5-(4-tert-butylphenyl)-1,3,4-oxadiazole and 2,2',2"-(1,3,5-benzenetriyl)tris-[1-phenyl-1H-benzimidazole], 3-phenyl-4(1' napthyl)-5-phenyl-1,2,4-triazole (TAZ), 1,3,4-oxadiazole,2,2'-(1,3-phenylene)bis[5-[4-(1,1-dimethylethyl) phenyl]] (OXD-7) or poly[2-(6-cyano-6-methyl)heptyloxy-1,4-phenylene(CNPP), AlOq, Alq(Clq)2, Al(Saph-q), Al(ODZ)3, Ph2Bq, Zn(BIZ)2, Bepp2, Bebq2, Zn(ODZ)2, spiro-PBD, or BMB-3T.

Each of the above layers may be for example, from about 0.1 nm to about 200 nm thick or from about 10 nm to about 100 nm thick.

Device 400 may optionally include a hole blocking layer 460 between the emissive layer 410 and the cathode 430. Particularly, the hole blocking layer 460 is disposed between the electron transporting layer 450 and the cathode 430, if present in device 400.

Generally, the efficiency of OLED devices may be improved by incorporating a hole blocking layer. Without being limited to any particular theory, it is believed that the HOMO level of the hole blocking material prevents the charges from diffusing out of the emissive layer but the hole blocking material has a sufficiently low electron barrier to allow electrons to pass through the hole blocking layer and enter the emissive layer (see, for example, U.S. Pat. No. 6,097,147; U.S. Pat. No. 6,784,106 and US 20030230980).

The hole blocking layer 460 comprises a hole blocking material. Hole blocking materials are known to a person skilled in the art, and include, for example, 2,9-dimethyl-4,7-diphenyl-1,10-phenanthroline (BCP) and 1,3,5-tris(phenyl-2-benzimidazolyl)benzene (TPBI). Typically, hole blocking layer 460 is thinner than the electron transporting layer 450, and may have a thickness for example of about 5 nm to about 30 nm.

Device 400 may optionally include an electron injecting layer 470 disposed immediately before the cathode 430. The electron injecting layer 470 comprises an electron injecting material, which is any material that can efficiently transfer electrons from the cathode 430 to electron transporting layer 450. Electron injecting materials are known to a person skilled in the art and include, for example, lithium fluoride or lithium fluoride/aluminium. The electron injecting layer 470 generally may have a thickness much smaller than the thickness of the cathode 430 or of the adjacent electron transporting layer 450 and may have a thickness for example of about 0.5 nm to about 5.0 nm.

As with device 300, device 400 may be deposited or formed on a support.

As will be appreciated, the device may be prepared by combining different layers in different ways, and other layers not specifically described or depicted in device 400 may also be present.

As well, it will be appreciated that a material may serve more than one function in an electroluminescent device. Due to the ambipolar charge transporting nature of the compounds of formula (I), these compounds may be found in other layers in the described devices. For example, a compound of formula (I) may constitute, alone or as part of a mixture, the hole transporting layer, or the electron transporting layer.

Thus, the presently described devices include devices in which at least one of a hole transporting layer, an emissive layer, a hole blocking layer and an electron transporting layer comprises a compound of formula (I).

The above-mentioned devices may be prepared by layering the relevant layers on top of one another. The layers may be prepared by methods known in the art, including solution coating techniques mentioned above. Solution coating steps may be carried out in an inert atmosphere, such as, for example, under nitrogen gas. Alternatively, layers may be prepared by thermal evaporation or by vacuum deposition. Metallic layers may be prepared by known techniques, such as, for example, thermal or electron-beam evaporation, chemical-vapour deposition or sputtering.

EXAMPLES

Instruments

Nuclear magnetic resonance (NMR) spectra were collected on a Bruker DPX 400 MHz spectrometer using chloroform-d as a solvent and tetramethylsilane (TMS) as an internal standard. Matrix-Assisted Laser Desorption/Ionization Time-Of-Flight (MALDI-TOF) mass spectra were obtained on a Bruker Autoflex TOF/TOF instrument. High Performance Liquid Chromatography (HPLC) was conducted on a Waters 2695 separation module combined with a Waters 2996 photodiode array detector. Differential scanning calorimetry (DSC) was carried out under nitrogen on a TA Instrument DSC 2920 module (scanning rate of 20° C./min). Thermal gravimetric analysis (TGA) was carried out using a TA Instrument TGA 2050 module (heating rate of 20° C./min). Cyclic voltammetry (CV) experiments were performed on an Autolab potentiostat (model PGSTAT30). All CV measurements were recorded in dichloromethane with 0.1 M tetrabutylammonium hexafluorophosphate as supporting electrolyte (scan rate of 50 mV/s) using a conventional three electrode configuration consisting of a platinum wire working electrode, a gold counter electrode, and a Ag/AgCl in 3 M KCl reference electrode. The measured potentials were converted to SCE (saturated calomel electrode) and the corresponding ionization potential (IP) and electron affinity (EA) values were derived from the onset redox potentials, based on −4.4 eV as the SCE energy level relative to vacuum (EA=Ered-onset+4.4 eV, IP=Eox-onset+4.4 eV). The absorption and photoluminescent spectra were obtained using a Shimadzu UV-3101 PC UV-vis-NIR spectrophotometer and a Perkin-Elmer LS-50B luminescence spectrophotometer with a xenon lamp as light source. The solution spectra were measured from dichloromethane solution.

Synthesis

Figure 2:
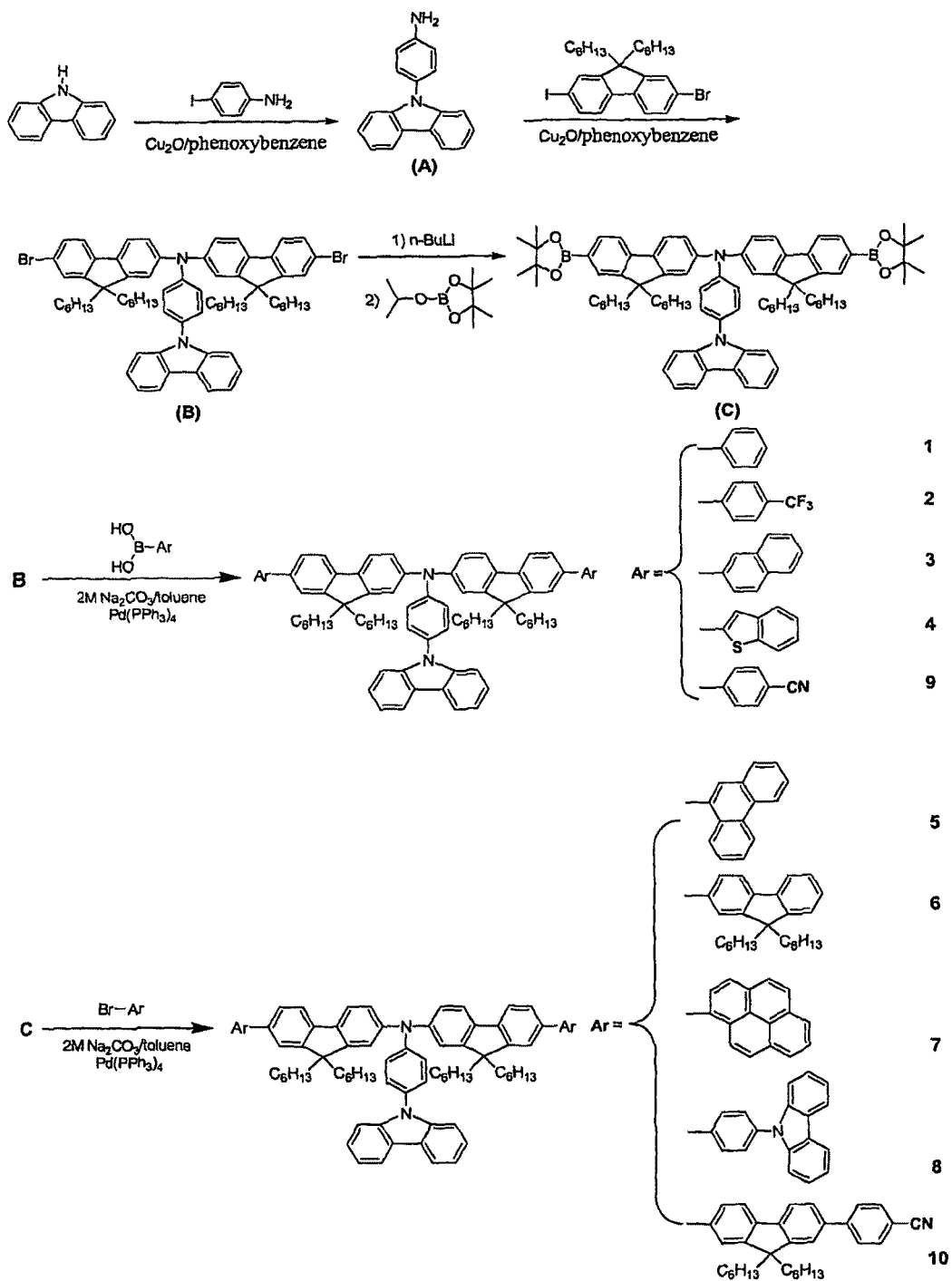
FIG. 2 is a schematic diagram setting out a synthesis mechanisms for certain compounds of formula (I)

The synthesis methods described below are depicted in the synthesis schematic depicted in FIG. 2.

Synthesis of 9-(4-bromophenyl)carbazole 9-(4-bromophenyl) carbazole was prepared through the Ullmann Reaction following the procedures reported in the literature (*Macromolecules* 2004, 37, 5531-5537). Briefly, a mixture of 1-bromo-4-iodobenzene (2.83 g, 10 mmol), copper (I) oxide (2.86 g, 20 mmol) and carbazole (0.84 g, 5 mmol) in 10 ml N,N-dimethylacetamide (DMAC) was heated to reflux in an oil bath for 24 h under $N_2$ atmosphere. The reaction mixture was cooled to room temperature and then filtered to remove excess copper complex. The filtrate was evaporated to dryness and went through silica gel column to give product, yielding 1.22 g (76%). $^1$H NMR (400 MHz, CDCl$_3$): δ(ppm) 8.132-8.122 (d, J=8.0 Hz, 2H), 7.715-7.695 (t, J=8.0 Hz, 2H), 7.476-7.247 (m, 8H).

Synthesis of 4-(2-bromo-9,9-dihexyl-9H-fluoren-7-yl)benzonitrile 4-(2-bromo-9,9-dihexyl-9H-fluoren-7-yl)benzonitrile was prepared through the following procedure. A mixture of 2,7-dibromo-9,9-dihexyl-9H-fluorene (0.985 g, 2 mmol), 4-cyanophenylboronic acid (0.146 g, 1 mmol), and tetrakis(triphenylphosphine) palladium (11.6 mg, 0.01 mmol) were added to an air-free two-phase mixture of toluene (25 mL) and aqueous 2M $Na_2CO_3$ solution (15 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.27 g of pure product were obtained by recrystallization in heptane with a yield of 51%. $^1$H NMR (400 MHz, CDCl$_3$): δ(ppm) 7.766-7.751 (m, 5H), 7.605-7.583 (d, J=8.8 Hz, 1H), 7.583-7.564 (d, J=7.6 Hz, 1H), 7.524 (s, 1H), 7.495-7.476 (m, 2H), 2.013-1.964 (m, 4H), 1.140-1.053 (m, 12H), 0.781-0.746 (t, J=7.0 Hz, 6H), 0.658-0.624 (m, 4H).

Synthesis of 4-(9H-carbazol-9-yl)benzenamine (A)

4-(9H-carbazol-9-yl)benzenamine (A) was prepared through the Ullmann Reaction following the procedures reported in the literature (*Macromolecules* 2004, 37, 5531-5537). A mixture of 4-iodobenzenamine (2.19 g, 10 mmol), copper (I) oxide (2.18 g, 20 mmol) and carbazole (3.35 g, 20 mmol) in 40 ml 1-phenoxybenzene was heated to 190° C. in an oil bath for 24 h under N$_2$ atmosphere. The reaction mixture was cooled to room temperature and then filtered by fast silica gel column to remove excess copper complex and 1-phenoxybenzene. The filtrate was evaporated to dryness and passed through a silica gel column using hexane and ethyl acetate mixture (6:1) as eluent to give product, yielding 2.37 g (92%). $^1$H NMR (400 MHz, CDCl$_3$): δ(ppm) 8.164-8.144 (d, J=8.0 Hz, 2H), 7.432-7.395 (t, J=8.0 Hz, 2H), 7.353-7.277 (m, 6H), 6.912-6.891 (d, J=7.6 Hz, 2H), 4.019 (w, 2H).

Synthesis of Compound (B)

Compound (B) was prepared following the above procedure. A mixture of 2-bromo-9,9-dihexyl-7-iodo-9H-fluorene (17.26 g, 32 mmol), copper (I) oxide (2.29 g, 16 mmol) and (A) (2.07 g, 8 mmol) in 1-phenoxybenzene was heated to 210° C. in an oil bath for 24 h under N$_2$ atmosphere. The reaction mixture was cooled to room temperature and then filtered to remove excess copper complex. The filtrate was evaporated to dryness and passed through a silica gel column to give product, yielding 4.35 g (50%). $^1$H NMR (400 MHz, CDCl$_3$): δ(ppm) 8.190-8.171 (d, J=7.7 Hz, 2H), 7.625-7.605 (d, J=8.0 Hz, 2H), 7.531-7.440 (m, 12H), 7.351-7.263 (m, 6H), 7.175-7.157 (d, J=7.6 Hz, 2H), 1.936-1.898 (m, 8H), 1.174-1.109 (m, 24H), 0.810-0.776 (t, J=7.2 Hz, 12H), 0.726 (m, 8H)

Synthesis of Compound (C)

Compound (C) was prepared through the following procedure. To a solution of (B) (2.16 g, 2 mmol) in anhydrous THF (40 mL) at −78° C. was added n-butyllithium (5 mL, 8 mmol, 1.6M in hexane). The mixture was stirred at −78° C. for 1 h. 2-isopropoxy-4,4,5,5-tetramethyl-1,3,2-dioxaborolane (2.4 mL, 12 mmol) was added rapidly to the solution. The mixture was allowed to warm to room temperature and stirred overnight. The mixture was then poured into water and extracted with diethyl ether. The organic extracts were combined and washed with brine and dried with anhydrous MgSO$_4$. The solvent was removed under reduced pressure, and the crude product was purified by recrystallization from a hexane/chloroform mixture to afford product, yielding 1.36 g (58%). $^1$H NMR (400 MHz, CDCl$_3$): δ (ppm) 8.186-8.166 (d, J=8.0 Hz, 2H), 7.620-7.601 (d, J=7.6 Hz, 2H), 7.505-7.435 (m, 12H), 7.334-7.257 (m, 6H), 7.168-7.149 (d, J=7.6 Hz, 2H), 1.930-1.893 (m, 8H), 1.589 (s, 24H), 1.168-1.104 (m, 24H), 0.804-0.770 (t, J=7.2 Hz, 12H), 0.722 (m, 8H)

Synthesis of Compound 1

A mixture of (B) (0.162 g, 0.15 mmol), phenylboronic acid (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.134 g of pure compound 1 was obtained by recrystallization in heptane with a yield of 83%. $^1$NMR (400 MHz, CDCl$_3$): δ (ppm) 8.154 (d, 2H), 7.675 (m, 8H), 7.578 (m, 6H), 7.479 (m, 10H), 7.358 (m, 4H), 7.251 (m, 4H), 1.977 (m, 8H), 1.092 (m, 24H), 0.763 (m, 20H). MS (MALDI): m/z=1074.79 (calcd. for C$_{80}$H$_{86}$N$_2$:1074.68). Anal. Found: C, 89.03; H, 8.05; N, 2.73 (calcd.: C, 89.34; H, 8.06; N, 2.60).

Synthesis of Compound 2

A mixture of (B) (0.162 g, 0.15 mmol), 4-trifluoromethylphenylboronic acid (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.115 g of pure compound 2 was obtained by recrystallization in heptane with a yield of 63%. $^1$H NMR (400 MHz, CDCl$_3$): δ (ppm) 8.163 (d, 2H), 7.769 (m, 6H), 7.734 (m, 6H), 7.759 (d, 2H), 7.548 (m, 2H), 7.453 (m, 6H), 7.307 (m, 6H), 7.197 (m, 2H), 1.977 (m, 8H), 1.106 (m, 24H), 0.768 (m, 20H). MS (MALDI): m/z=1210.77 (calcd. for C$_{82}$H$_{84}$F$_6$N$_2$:1210.65). Anal. Found: C, 81.32; H, 6.81; N, 2.29 (calcd.: C, 81.29; H, 6.99; N, 2.31).

Synthesis of Compound 3

A mixture of (B) (0.162 g, 0.15 mmol), 2-naphthylboronic acid (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.104 g of pure compound 3 were obtained by recrystallization in heptane with a yield of 59%. $^1$H NMR (400 MHz, CDCl$_3$): δ (ppm) 8.177 (d, 2H), 8.124 (m, 2H), 7.947 (m, 6H), 7.900 (d, 2H), 7.853 (d, 2H), 7.732 (m, 8H), 7.511 (m, 12H), 7.323 (m, 4H), 2.041 (m, 8H), 1.127 (m, 24H), 0.776 (m, 20H). MS (MALDI): m/z=1174.83 (calcd. for C$_{88}$H$_{90}$N$_2$:1174.71). Anal. Found: C, 89.58; H, 7.31; N, 2.38 (calcd.: C, 89.90; H, 7.72; N, 2.38).

Synthesis of Compound 4

A mixture of (B) (0.162 g, 0.15 mmol), 3-benzothiophenylboronic acid (0.6 mmol), and tetrakis(triphenylphosphine)

palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.98 g of pure compound 4 were obtained by recrystallization in heptane with a yield of 55%. $^1$H NMR (400 MHz, CDCl$_3$): δ (ppm) 8.174-8.155 (d, J=7.6 Hz, 2H), 7.858-7.838 (d, J=8.0 Hz, 2H), 7.801-7.782 (d, J=7.6 Hz, 2H), 7.704-7.617 (m, 10H), 7.489-7.450 (m, 6H), 7.367-7.274 (m, 10H), 7.220 (w, 2H), 1.987 (m, 8H), 1.111 (m, 24H), 0.782-0.749 (m, 20H). $^{13}$C NMR (400 MHz, CDCl$_3$): δ (ppm) 141.496, 141.290, 139.818, 126.222, 124.905, 124.585, 123.781, 122.581, 120.668, 120.241, 110.212, 55.706, 40.700, 31.938, 30.057, 24.330, 22.892, 14.323. MS (MALDI): m/z=1186.76 (calcd. for C$_{84}$H$_{86}$N$_2$S$_2$: 1186.62). Anal. Found: C, 84.86; H, 7.46; N, 2.45; S, 5.25 (calcd.: C, 84.94; H, 7.30; N, 2.36; S, 5.40).

Synthesis of Compound 5

A mixture of (C) (0.176 g, 0.15 mmol), 9-bromophenanthrene (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.129 g of pure compound 5 were obtained by recrystallization in heptane with a yield of 67%. $^1$H NMR (400 MHz, CDCl$_3$): δ (ppm) 8.804 (d, 2H), 8.746 (d, 2H), 8.162 (d, 2H), 8.798 (d, 2H), 7.934 (d, 2H), 7.780 (m, 4H), 7.695 (m, 8H), 7.526 (m, 8H), 7.458 (m, 6H), 7.248 (m, 6H), 1.979 (m, 8H), 1.147 (m, 24H), 0.866 (m, 8H), 0.793 (m, 12H). MS (MALDI): m/z=1274.89 (calcd. for C$_{96}$H$_{94}$N$_2$: 1274.74). Anal. Found: C, 90.54; H, 7.21; N, 2.21 (calcd.: C, 90.38; H, 7.43; N, 2.20).

Synthesis of Compound 6

A mixture of (C) (0.176 g, 6.15 mmol), 2-bromo-9,9-dihexylfluorene (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.157 g of pure compound 6 were obtained by recrystallization in heptane with a yielding of 66%. $^1$H NMR (400 MHz, CDCl$_3$): δ (ppm) 8.177 (d, 2H), 7.794 (d, 2H), 7.750 (d, 4H), 7.664 (m, 6H), 7.621 (m, 4H), 7.453 (m, 8H), 7.362 (m, 6H), 7.335 (m, 6H), 2.036 (m, 18H), 1.126 (m, 48H), 0.771 (m, 40H). MS (MALDI): m/z=1587.28 (calcd.: for C$_{118}$H$_{142}$N$_2$:1587.12). Anal. Found: C, 89.43; H, 8.69; N, 1.78 (calcd.: C, 89.23; H, 9.01; N, 1.76).

Synthesis of Compound 7

A mixture of (C) (0.176 g, 0.15 mmol), 1-bromopyrene (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.108 g of pure compound 7 were obtained by recrystallization in heptane with a yield of 54%. $^1$H NMR (400 MHz, CDCl$_3$): δ (ppm) 8.271 (d, 2H), 8.260 (d, 2H), 8.206 (d, 2H), 8.182 (m, 2H), 8.170 (d, 2H), 8.121 (m, 4H), 8.099 (d, 2H), 8.046 (s, 2), 8.023 (m, 2H), 7.845 (m, 2H), 7.758 (d, 2H), 7.612 (m, 4H), 7.513 (m, 2H), 7.460 (m, 6H), 7.381 (m, 2H), 7.308 (m, 4H), 2.005 (m, 8H), 1.169 (m, 24H), 0.905 (m, 8H), 0.806 (t, 12H). MS (MALDI): m/z=1323.92 (calcd. for C$_{100}$H$_{94}$N$_2$:1323.74). Anal. Found: C, 90.65; H, 7.02; N, 2.13 (calcd.: C, 90.73; H, 7.16; N, 2.12).

Synthesis of Compound 8

A mixture of (C) (0.176 g, 0.15 mmol), 9-(4-bromophenyl) carbazole (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.118 g of pure compound 8 were obtained by recrystallization in heptane with a yield of 56%. $^1$H NMR (400 MHz, CDCl$_3$): δ (ppm) 8.184 (d, 6H), 7.907 (m, 4H), 7.692 (m, 10H), 7.516-7.425 (m, 18H), 7.315 (t, 10H), 2.022 (m, 8H), 1.134 (m, 24H), 0.785 (m, 20H). MS (MALDI): m/z=1404.96 (calcd. for C$_{104}$H$_{100}$N$_4$:1404.79). Anal. Found: C, 88.74; H, 7.01; N, 3.98 (calcd.: C, 88.85; H, 7.17; N, 3.98).

Synthesis of Compound 9

A mixture of (B) (0.162 g, 0.15 mmol), 4-cyanophenylboronic acid (0.6 mmol), and tetrakis(triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.147 g of pure compound 9 were obtained by recrystallization in heptane with a yield of 87%. $^1$H NMR (400 MHz, CDCl$_3$): δ (ppm) 8.172 (d, 2H), 7.758 (m, 10H), 7.683 (d, 2H), 7.592 (d, 2H), 7.534 (s, 2H), 7.460 (m, 6H), 7.366 (m, 2H), 7.301 (m, 4H), 7.198 (m, 2H), 1.980 (m, 8H), 1.095 (m, 24H), 0.756 (m, 20H). MS (MALDI): m/z=1124.76 (calcd. for C$_{82}$H$_{84}$N$_4$:1124.67). Anal. Found: C, 87.34; H, 7.33; N, 5.06 (calcd.: C, 87.50; H, 7.52; N, 4.98).

Synthesis of Compound 10

A mixture of (C) (0.176 g, 0.15 mmol), 2-bromo-7-(4'-cyanophenyl)-9,9-dihexylfluorene (0.6 mmol), and tetrakis (triphenylphosphine) palladium (3.4 mg, 0.003 mmol) were added to an air-free two-phase mixture of toluene (15 mL) and an aqueous 2M Na$_2$CO$_3$ solution (12 mL). The resulting mixture was vigourously stirred under argon atmosphere at 110° C. for 24 hours. The organic layer was separated and the aqueous phase was extracted with ether. The organic layers were washed with brine (2×50 mL), and dried with anhydrous MgSO$_4$. The solvent was evaporated and the residue passed through a silica-gel column. 0.160 g of pure compound 10 were obtained by recrystallization in heptane with a yield of 60%. $^1$H NMR (400 MHz, CDCl$_3$): δ (ppm) 8.183-8.163 (d, J=8.0 Hz, 2H), 7.843-7.824 (d, J=7.6 Hz, 4H), 7.777-7.745 (m, 10H), 7.707-7.582 (m, 14H), 7.527-7.506 (d, J=8.4 Hz, 2H), 7.460-7.447 (m, 4H), 7.396-7.376 (d, J=8.0 Hz, 2H), 7.343-7.293 (m, 4H), 7.231-7.210 (d, J=8.4 Hz, 2H), 2.106 (m, 16H), 1.141 (m, 48H), 0.800-0.755 (m, 40H). $^{13}$C NMR (400 MHz, CDCl$_3$): δ (ppm) 153.075, 152.502, 152.279, 151.876, 147.906, 147.266, 146.589, 142.027, 141.578, 140.618, 140.239, 139.780, 138.230, 136.934, 132.958, 131.715, 128.102, 126.675, 126.237, 124.306, 123.866, 121.962, 121.049, 120.668, 120.199, 119.994, 119.878, 119.356, 111.088, 110.197, 55.852, 55.708, 40.716, 31.947, 31.809, 30.063, 24.364, 24.237, 22.884, 14.339. MS (MALDI): m/z=1789.42 (calcd. for C$_{132}$H$_{148}$N$_4$:1789.17). Anal. Found: C, 88.62; H, 8.25; N, 3.14 (calcd.: C, 88.54; H, 8.33; N, 3.13).

Device Fabrication and Measurement

Two types of devices have been fabricated and evaluated based on the following configuration.

Configuration A

ITO/PEDOT:PSS/PVK:dopant/TPBI/LiF/Ca/Ag 1.2 mg of the relevant emitting dopant (compounds of formula (I) synthesized as described above) and 60 mg poly (9-vinylcarbazole) (PVK) were dissolved in 4 ml of ethyl benzoate and filtered through a 0.2 mm PTFE filter for device fabrication.

The light-emitting devices were prepared on patterned indium tin oxide (ITO) coated glass substrates. The substrates were cleaned and treated with oxygen plasma and spin-coated with 50 nm of poly(3,4-ethylenedioxythiophene) (PEDOT) doped with poly(styrenesulfonic acid) (PSS), followed by drying at 120° C. in air for 15 min.

The polymer solutions were spin-coated to form the emitting layer with a thickness of about 70 nm and transferred into a chamber under vacuum of 1×10$^{-5}$ Pa. A 40 nm 1,3,5-tris (phenyl-2-benzimidazolyl)benzene (TPBI) was deposited onto the surface of the emitting layer for electron injection and hole blocking.

The cathode was composed of 0.4 nm LiF, 20 nm Ca and 200 nm Ag, which were thermal deposited sequentially.

All the measurements were carried out in air at room temperature. The current-voltage, current-luminance characteristics of the devices were recorded using a Keithley 2420 source meter and a calibrated photodiode. EL spectra were recorded with an Ocean Optics USB2000 miniature fiber optic spectrometer. The photometric data were calculated using current-voltage-luminance data and EL spectra of the devices.

Figure 5:
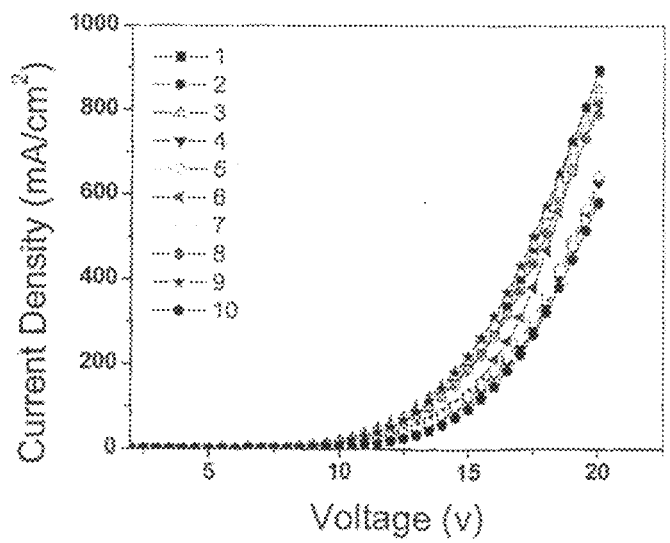
FIG. 5 is an I-V plot of devices with the configuration of ITO/PEDOT:PSS/PVK:dopant/TPBI/LiF/Ca/Ag, where the dopant is various compounds of formula (I)
Figure 6:
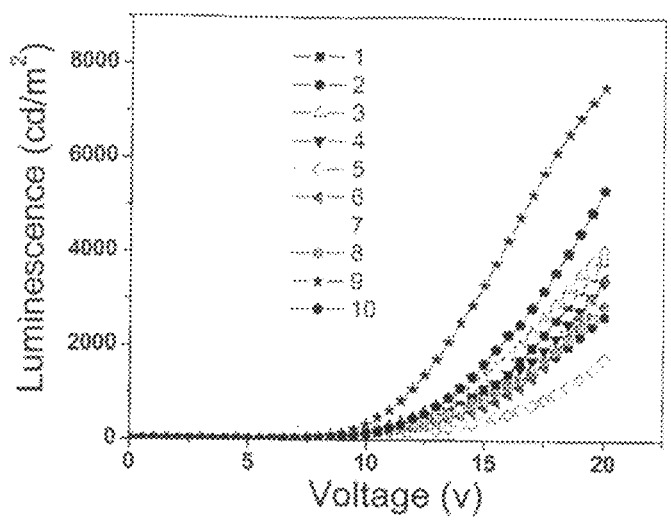
FIG. 6 is a V-L plot of devices with the configuration of ITO/PEDOT:PSS/PVK:dopant/TPBI/LiF/Ca/Ag.

The device performance of devices containing compounds 1 to 10 is summarized in Table 1. FIGS. 5 and 6 are I-V and V-L plots of devices of configuration A.

TABLE 1

Summary of the device performance of compound 1 to 10 with device configuration A

| Compound | Turn-on (V) | Voltage at 100 cd/m² (V) | Max. Curr. Eff. (cd/A) | Max. EQE (%) | $\lambda_{max}$ EL (nm) | CIE (x, y) |
|---|---|---|---|---|---|---|
| 1 | 5.4 | 9.4 | 1.25 | 2.12 | 426 | 0.160, 0.085 |
| 2 | 6.2 | 10.4 | 1.19 | 1.20 | 440 | 0.180, 0.131 |
| 3 | 5.5 | 9.0 | 1.21 | 1.84 | 434 | 0.155, 0.089 |
| 4 | 5.6 | 9.9 | 1.55 | 1.93 | 442 | 0.151, 0.106 |
| 5 | 6.4 | 11.0 | 0.73 | 0.99 | 433 | 0.157, 0.099 |
| 6 | 5.9 | 10.0 | 1.71 | 1.64 | 432 | 0.205, 0.158 |
| 7 | 5.9 | 9.9 | 1.57 | 1.97 | 440 | 0.150, 0.108 |
| 8 | 6.1 | 9.8 | 0.99 | 1.18 | 436 | 0.163, 0.110 |
| 9 | 5.1 | 8.5 | 2.49 | 2.30 | 448 | 0.152, 0.148 |
| 10 | 5.3 | 9.6 | 3.50 | 3.40 | 446 | 0.178, 0.160 |

Configuration B

TO/PEDOT:PSS/Light Emitting Molecules/TPBI/LiF/Ca/Ag 60 mg of light emitting molecules, synthesized as described above, were dissolved in 4 ml of ethyl benzoate and filtered through a 0.2 mm PTFE filter for device fabrication.

The light-emitting devices were prepared on patterned indium tin oxide (ITO) coated glass substrates. The substrates were cleaned and treated with oxygen plasma and spin-coated with 50 nm of poly(3,4-ethylenedioxythiophene) (PEDOT) doped with poly(styrenesulfonic acid) (PSS), followed by drying at 120° C. in air for 15 min.

The light emitting molecular solutions were spin-coated to form the emitting layer with a thickness of about 70 nm and transferred into a chamber under vacuum of 1×10$^{-5}$ Pa. A 40 nm 1,3,5-tris(phenyl-2-benzimidazolyl)benzene (TPBI) was deposited onto the surface of the emitting layer for electron injection and hole blocking.

The cathode was composed of 0.4 nm LiF, 20 nm Ca and 200 nm Ag, which were thermal deposited sequentially.

Figure 7:
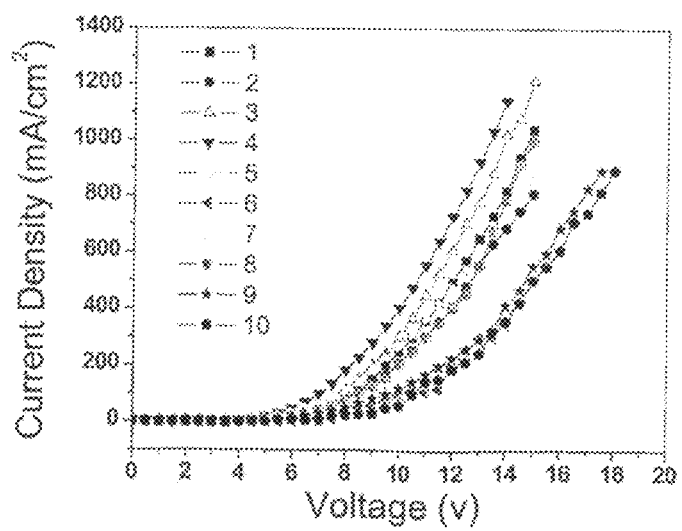
FIG. 7 is an I-V plot of devices with the configuration of ITO/PEDOT:PSS/compound/TPBI/LiF/Ca/Ag, where the compound is various compounds of formula (I)
Figure 8:
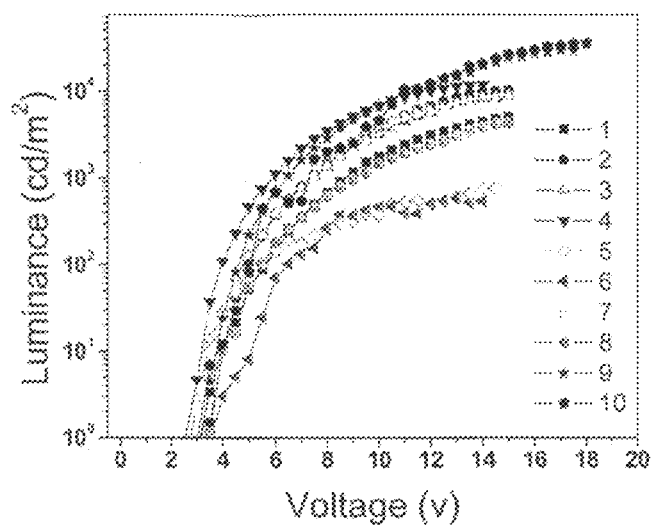
FIG. 8 is a V-L plot of devices with the configuration of ITO/PEDOT:PSS/compound/TPBI/LiF/Ca/Ag.
Figure 9:
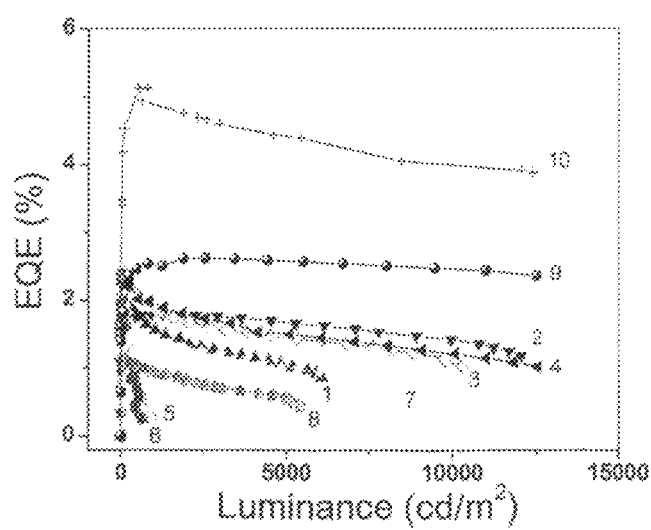
FIG. 9 is a plot of external quantum efficiency vs luminance of devices with the configuration of ITO/PEDOT:PSS/compound/TPBI/LiF/Ca/Ag.
Figure 10:
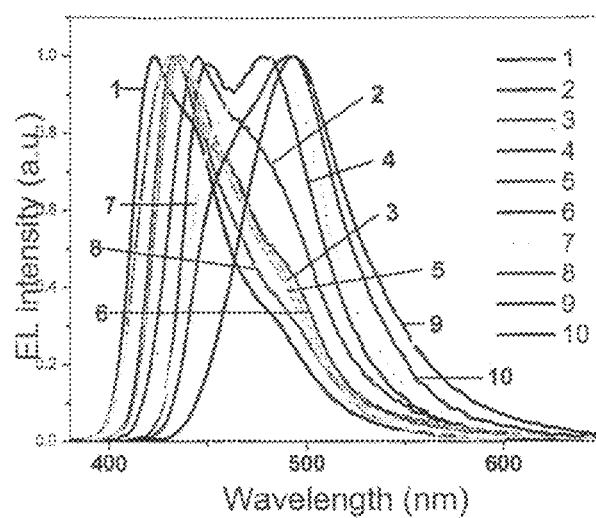
FIG. 10 is EL spectra of devices with a configuration of ITO/PEDOT:PSS/compound/TPBI/LiF/Ca/Ag.
Figure 11:
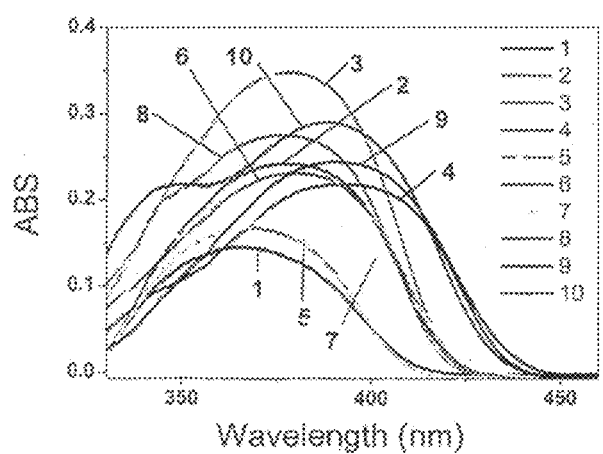
FIG. 11 is UV absorbance spectra for various compounds of formula (I) dissolved in chloroform.
Figure 12:
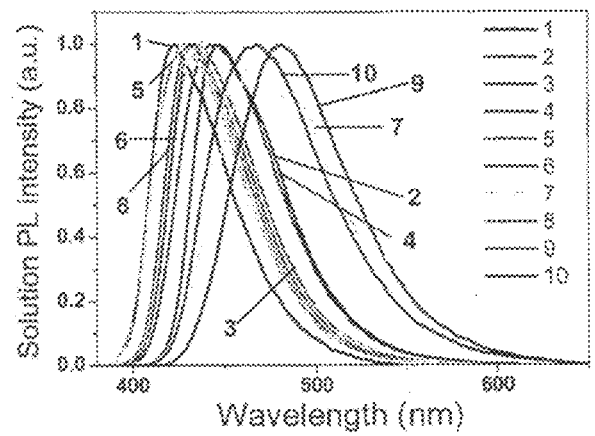
FIG. 12 is a graph of the photoluminescence of various compounds of formula (I) measured in chloroform.
Figure 13:
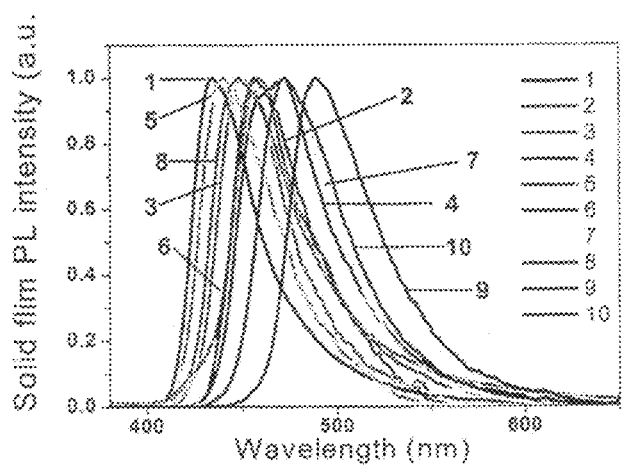
FIG. 13 is a graph of the photoluminescence of various compounds of formula (I) measured in the solid state after spin coating chloroform solutions containing the compounds onto a quartz plate.

The device performance of devices containing compounds 1 to 10 is summarized in Table 2. FIGS. 7 and 8 are I-V and V-L plots of devices of configuration B. FIG. 9 is a plot of external quantum efficiency vs luminance of devices of configuration B and FIG. 10 depicts EL spectra of devices having configuration B.

TABLE 2

Summary of device performance of compound 1 to 10 with device configuration B

| Compound | Turn-on (V) | Voltage at 100 cd/m² (V) | Max. Curr. Eff. (cd/A) | Max. EQE (%) | $\lambda_{max}$ EL (nm) | CIE (x, y) |
|---|---|---|---|---|---|---|
| 1 | 3.0 | 5.6 | 1.2 | 2.3 | 423 | 0.155, 0.070 |
| 2 | 3.3 | 4.9 | 1.9 | 1.8 | 446 | 0.152, 0.137 |
| 3 | 2.8 | 4.8 | 1.7 | 2.4 | 434 | 0.147, 0.085 |
| 4 | 2.7 | 3.9 | 2.9 | 2.4 | 450/477 | 0.143, 0.174 |
| 5 | 2.8 | 5.4 | 1.3 | 2.0 | 432 | 0.150, 0.084 |
| 6 | 3.5 | 6.5 | 1.3 | 2.0 | 433 | 0.151, 0.097 |
| 7 | 2.9 | 4.2 | 2.1 | 1.4 | 483 | 0.144, 0.215 |
| 8 | 3.4 | 5.5 | 0.9 | 1.2 | 436 | 0.162, 0.102 |
| 9 | 3.1 | 4.6 | 5.8 | 2.6 | 493 | 0.176, 0.397 |
| 10 | 3.0 | 5.1 | 9.1 | 5.1 | 492 | 0.144, 0.279 |

Table 3 depicts the energy levels of compounds 1 to 10.

TABLE 3

| Energy levels of light emitting materials compounds 1-10 | | | | | | | | | | |
|---|---|---|---|---|---|---|---|---|---|---|
| Compound | 1 | 2 | 3 | 4 | 5 | 6 | 7 | 8 | 9 | 10 |
| HOMO (eV) | −5.11 | −5.16 | −5.10 | −5.12 | −5.14 | −5.08 | −5.14 | −5.13 | −5.17 | −5.03 |
| LUMO (eV) | −2.15 | −2.26 | −2.20 | −2.31 | −2.14 | −2.18 | −2.28 | −2.21 | −2.39 | −2.22 |
| Bandgap (eV) | 2.96 | 2.90 | 2.90 | 2.81 | 3.00 | 2.90 | 2.86 | 2.92 | 2.78 | 2.81 |

As can be understood by one skilled in the art, many modifications to the exemplary embodiments described herein are possible. The invention, rather, is intended to encompass all such modification within its scope, as defined by the claims.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

What is claimed is:

1. A compound of formula (I):

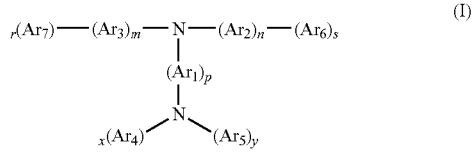

wherein:

Ar$_1$ is phenylene;

Ar2 and Ar3 are both 9,9-dialkylfluorenylene;

Ar$_4$ and Ar$_5$ are both phenylene and are connected to each other by a single bond;

Ar$_6$ and Ar$_7$ are the same and both are phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl, 7-(4'-cyanophenyl)-9,9-dihexylfluorenyl or any one of the following groups:

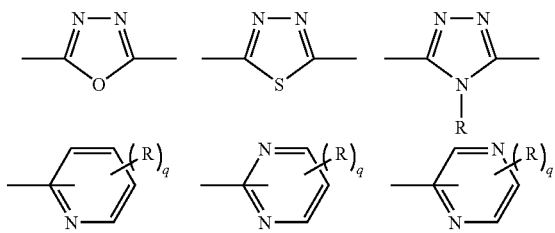

-continued

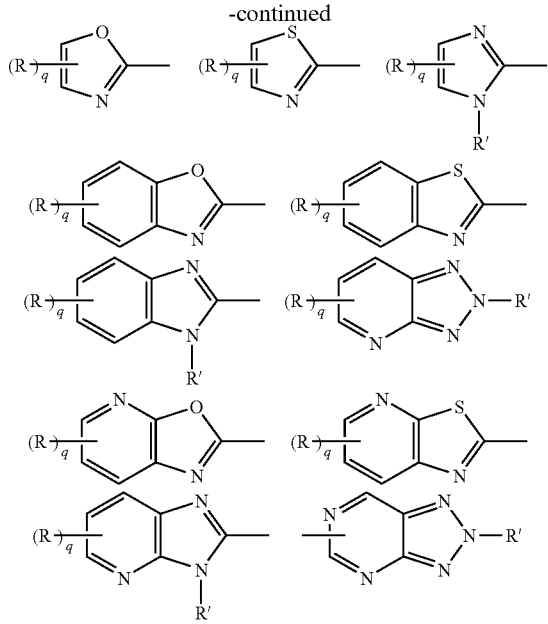

wherein each of R, R', R" and R'" is independently halo, cyano, nitro, carbonyl, thionyl, sulphonyl, alkyl, perfluoroalkyl, alkoxy, aryl, arylene vinylene, or arylene ethynylene, and q is an integer from 0 to 6, wherein alkyl is a branched or unbranched monovalent hydrocarbon group, having 1 to 18 carbon atoms;
and
each of m, n, p, r, s, x and y is 1.

2. The compound of claim 1 wherein $Ar_6$ and $Ar_7$ are the same and both are phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl, 7-(4'-cyanophenyl)-9,9-dihexylfluorenyl or any one of the following groups:

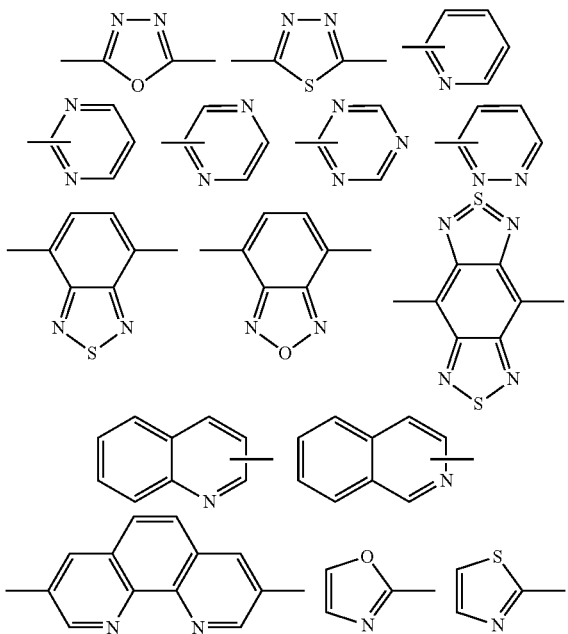

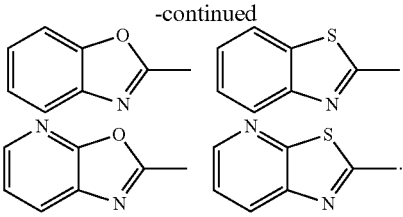

3. The compound of claim 1 wherein $Ar_6$ and $Ar_7$ are the same and both are phenyl, 4-trifluoromethylphenyl, 2-naphthyl, 3-benzothiophenyl, phenanthrenyl, 9,9-dihexylfluorenyl, pyrenyl, 9-phenylcarbazolyl, 4-cyanophenyl or 7-(4'-cyanophenyl)-9,9-dihexylfluorenyl.

4. The compound of claim 1 wherein $Ar_6$ and $Ar_7$ are the same and both are any one of the following groups:

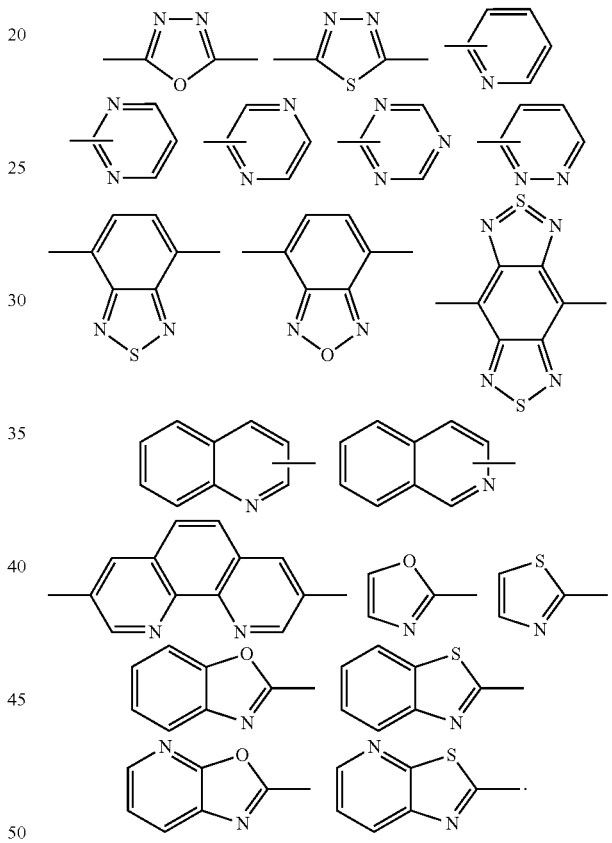

5. The compound of claim 1 wherein the 9,9-dialkylfluorenylene is 9,9-dihexylfluorenylene.

6. The compound of claim 1 wherein $Ar_6$ and $Ar_7$ are phenyl.

7. The compound of claim 1 wherein $Ar_6$ and $Ar_7$ are 4-trifluoromethylphenyl.

8. The compound of claim 1 wherein $Ar_6$ and $Ar_7$ are 2-naphthyl.

9. The compound of claim 1 wherein $Ar_6$ and $Ar_7$ are 3-benzothiophenyl.

10. The compound of claim 1 wherein $Ar_6$ and $Ar_7$ are phenanthrenyl.

11. The compound of claim 1 wherein $Ar_6$ and $Ar_7$ are 9,9-dihexylfluorenyl.

12. The compound of claim 1 wherein $Ar_6$ and $Ar_7$ are pyrenyl.

13. The compound of claim 1 wherein $Ar_6$ and $Ar_7$ are 9-phenylcarbazolyl.

14. The compound of claim 1 wherein $Ar_6$ and $Ar_7$ are 4-cyanophenyl.

15. The compound of claim 1 wherein $Ar_6$ and $Ar_7$ are 7-(4'-cyanophenyl)-9,9-dihexylfluorenyl.

16. A thin film comprising a compound according to claim 1.

17. The thin film of claim 16 further comprising a host material.

18. The thin film of claim 17 wherein the host material comprises poly(9-vinylcarbazole), 4,4'-N,N'-dicarbazole-biphenyl, 4,4',4"-tri(N-carbazole)triphenylamine, N,N'-diphenyl-N,N'-bis(3-methylphenyl)(1,1'-biphenyl)-4,4'-diamine, N,N'-bis(1-naphthyl)-N,N'-diphenyl-1,1"-biphenyl-4,4'-diamine, 4,4',4"-tris(N,N-diphenyl-amino)triphenylamine, 1,3,5-tris(diphenylamino)benzene, 1,3,5-tris(4-(di-2-pyridylamino)phenyl)benzene, poly(1,4-phenylenevinylene) derivatives, polyfluorene derivatives, 3-phenyl-4(1' napthyl)-5-phenyl-1,2,4-triazole, 2-(4-biphenyl)-5(4-tertbutyl-phenyl)-1,3,4,oxadiazole, 1,3,4-oxadiazole,2,2'-(1,3-phenylene)bis[5-[4-(1,1-dimethylethyl)phenyl], or poly[2-(6-cyano-6-methyl)heptyloxy-1,4-phenylene.

19. The thin film of claim 16 wherein the compound serves as a host material, the thin film further comprising an organic dye or a phosphorescent emitter.

20. The thin film of claim 19 wherein the organic dye comprises 1042-benzothiazolyl)-1,1,7,7-tetramethyl-2,3,6,7-tetrahydro-1H,5H,11H-[1]benzo-pyrano[6,7,8-ij]quinolizin-11-one, 3-(2-benzothiazolyl)-7-(diethylamino)-2H-1-benzopyran-2-one, 4-(dicyanomethylene)-2-t-butyl-6-(1,1,7,7-tetramethyljulolidyl-9-enyl)-4H-pyran (DCJTB), rubrene, 4-(dicyanomethylene)-2-t-butyl-6-(p-diphenylaminostyryl)-4H-pyran (DCTP), 3-(dicyanomethylene)-5,5-dimethyl-1-[(4-dimethylamino)styryl]cyclohexene (DCDDC), 6-methyl-3-[3-(1,1,6,6-tetramethyl-10-oxo-2,3,5,6-tetrahydro-1H,4H,10H-[1-oxa-3a-azabenzo[de]-anthracen-9-yl)acryloyl]pyran-2,4-dione (AAAP), 6,13-diphenylpentacene (DPP) and 3-(N-phenyl-N-p-tolylamino)-9-(N-p-styrylphenyl-N-p-tolylamino)perylene[(PPA)(PSA)Pe-1], or 1,1'-dicyano-substituted bis-styrylnaphthalene derivative (BSN).

21. The thin film of claim 19 wherein the phosphorescent emitters comprises PtOEP or Ir(ppy)3.

22. The thin film of claim 16 prepared by solution coating.

23. A device comprising an anode, a cathode and a compound of claim 1 disposed between the anode and the cathode.

24. The device of claim 23 further comprising a hole injecting layer disposed adjacent to the anode, a hole transporting layer disposed adjacent to the hole injecting layer, an emissive layer disposed between the hole transporting layer and the cathode, an electron transporting layer disposed between the emissive layer and the cathode, a hole blocking layer disposed between the electron transporting layer and the cathode, and an electron injecting layer disposed between the hole blocking layer and the cathode, wherein at least one of the hole transporting layer, the emissive layer, or the electron transporting layer comprises the compound.

25. The device of claim 23 further comprising a hole transporting layer disposed adjacent to the anode, an emissive layer disposed between the hole transporting layer and the cathode, and an electron transporting layer disposed between the emissive layer and the cathode, wherein at least one of the hole transporting layer, the emissive layer, or the electron transporting layer comprises the compound.

26. The device of claim 23, wherein the compound is contained within a thin film.

27. The device of claim 23 comprising an emissive layer wherein said emissive layer comprises the compound.

28. The device of claim 27 further comprising a hole transporting layer disposed between the emissive layer and the anode.

29. The device of claim 28 wherein the hole transporting layer comprises polyaniline or a mixture of poly(3,4-ethylenedioxythiophene) and poly(styrenesulfonic acid).

30. The device of claim 27 further comprising a hole injecting layer disposed between the anode and the hole transporting layer.

31. The device of claim 30 wherein the hole injecting layer comprises 4,4'-N,N'-dicarbazole-biphenyl (CBP), 4,4',4"-tri(N-carbazole)triphenylamine (TCTA), N,N'-diphenyl-N,N'-bis(3-methylphenyl)(1,1'-biphenyl)-4,4'-diamine (TPD), N,N'-bis(1-naphthyl)-N,N'-diphenyl-1,1"-biphenyl-4,4'-diamine (NPB), poly(1,4-phenylenevinylene) or polyfluorene.

32. The device of claim 27 further comprising an electron transporting layer disposed between the emissive layer and the cathode.

33. The device of claim 32 wherein the electron transporting layer comprises aluminum tris(8-hydroxyquinoline), 2-(4-biphenyl)-5-(4-tert-butylphenyl)-1,3,4-oxadiazole and 2,2',2"-(1,3,5-benzenetriyl)tris-[1-phenyl-1H-benzimidazole], 3-phenyl-4(1'napthyl)-5-phenyl-1,2,4-triazole (TAZ), 1,3,4-oxadiazole,2,2'-(1,3-phenylene)bis[5-[4-(1,1-dimethylethyl)phenyl]] (OXD-7) or poly[2-(6-cyano-6-methyl)heptyloxy-1,4-phenylene(CNPP).

34. The device of claim 27 further comprising a hole blocking layer disposed between the emissive layer and the cathode.

35. The device of claim 34 wherein the hole blocking layer comprises 2,9-dimethyl-4,7-diphenyl-1,10-phenanthroline or 1,3,5-tris(phenyl-2-benzimidazolyl)benzene.

36. The device of claim 28 further comprising an electron injecting layer disposed immediately adjacent to the cathode, between the cathode and the emissive layer.

37. The device of claim 36 wherein the electron injecting layer comprises lithium fluoride or lithium fluoride/aluminium.

* * * * *

UNITED STATES PATENT AND TRADEMARK OFFICE
CERTIFICATE OF CORRECTION

PATENT NO. : 8,518,559 B2
APPLICATION NO. : 12/518089
DATED : August 27, 2013
INVENTOR(S) : Zhikuan Chen and Changgua Zhen It is certified that error appears in the above-identified patent and that said Letters Patent is hereby corrected as shown below:

In the Claims

Col. 25, Claim 20, line 28, "1042" should read -- 10-(2- --

Col. 25, Claim 20, line 37, "[1-oxa" should read -- 11-oxa --

Col. 26, Claim 36, line 48, "claim 28" should read -- claim 27 --

Signed and Sealed this
Sixth Day of January, 2015

Michelle K. Lee
*Deputy Director of the United States Patent and Trademark Office*